(12) United States Patent
Fukuma et al.

(10) Patent No.: US 7,566,132 B2
(45) Date of Patent: Jul. 28, 2009

(54) FUNDUS OBSERVATION DEVICE

(75) Inventors: Yasufumi Fukuma, Tokyo (JP);
Hiroyuki Otsuka, Tokyo (JP);
Kazuhiko Yumikake, Tokyo (JP);
Hiroaki Okada, Tokyo (JP); Yutaka Nishio, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 11/697,030

(22) Filed: Apr. 5, 2007

(65) Prior Publication Data

US 2007/0236660 A1 Oct. 11, 2007

(30) Foreign Application Priority Data

Apr. 7, 2006 (JP) ............... 2006-106935

(51) Int. Cl.
*A61B 3/10* (2006.01)
(52) U.S. Cl. .................. 351/221; 351/205; 351/208
(58) Field of Classification Search ......... 351/200–206, 351/208, 212, 245, 221
See application file for complete search history.

(56) References Cited

U.S. PATENT DOCUMENTS

| | | | | |
|---|---|---|---|---|
| 4,666,269 A | * | 5/1987 | Nakamura et al. | 351/212 |
| 6,244,710 B1 | | 6/2001 | Ogawa | 351/206 |
| 7,370,966 B2 | * | 5/2008 | Fukuma et al. | 351/205 |
| 2002/0176050 A1 | | 11/2002 | Shibata | 351/206 |
| 2003/0234908 A1 | | 12/2003 | Kushida | 351/206 |
| 2006/0066869 A1 | | 3/2006 | Ueno et al. | 356/497 |
| 2007/0146234 A1 | * | 6/2007 | Taira et al. | 345/6 |
| 2007/0182926 A1 | * | 8/2007 | Matsumoto | 351/206 |
| 2007/0236661 A1 | * | 10/2007 | Fukuma et al. | 351/205 |
| 2007/0296919 A1 | * | 12/2007 | Hideshima et al. | 351/221 |

FOREIGN PATENT DOCUMENTS

| | | |
|---|---|---|
| JP | 2003-000543 | 1/2003 |
| JP | 2004-350849 | 12/2004 |
| JP | 2005-241464 | 9/2005 |
| WO | 9737584 | 10/1997 |

OTHER PUBLICATIONS

European Search Report for EP 07 00 7261.

* cited by examiner

*Primary Examiner*—Mohammed Hasan
(74) *Attorney, Agent, or Firm*—Edwards Angell Palmer & Dodge LLP

(57) ABSTRACT

LCD 140 is provided for displaying an internal fixation target for fixating an eye E. Projection optical system (a part of an imaging optical system 120) is provided for projecting the displayed internal fixation target onto the a fundus oculi Ef. Image forming part 220 is provided for forming 2-dimensional images (images of fundus oculi) Ef of the surface of fundus oculi Ef. Display part 240A is provided for displaying images of fundus oculi Ef. Operation part 240B is provided for specifying the position of the displayed images of fundus oculi Ef. Main controller 211 is provided for changing the projection position of the internal fixation target on the fundus oculi by changing the display position of the fixation target by the LCD 140 based on the specified position. The image forming part 220 forms tomographic images of the fundus oculi Ef with the internal fixation target projected.

5 Claims, 12 Drawing Sheets

PRIOR ART

PRIOR ART

FUNDUS OBSERVATION DEVICE

BACKGROUND OF THE INVENTION

1. Field of the Invention

The present invention relates to a fundus observation device, for observing the state of the fundus oculi of an eye.

2. Description of the Related Art

As a fundus observation device, conventionally a fundus camera has been widely used. FIG. 11 shows one example of the appearance of a conventional fundus camera in general, and FIG. 12 shows one example of an optical system composition to be internally accommodated therein (e.g. JP Patent laid-open No. 2004-350849). Furthermore, "observation" is intended to include at least a case in which produced fundus images are observed (fundus observations with the naked eye may be included).

First, referring to FIG. 11, an explanation is made regarding the appearance of a conventional fundus camera 1000. This fundus camera 1000 is provided with a platform 3 mounted on a base 2 slidably in the front and rear, right and left (horizontal direction) directions. On this platform 3, an operation panel 3a and a control lever 4 are installed for an examiner to conduct various operations.

The examiner may place the platform 3 on the base 2 to be moved 3-dimensionally by operating the control lever 4. On the top of the control lever 4, an operation button 4a is installed to be pressed down to obtain fundus oculi images.

On the base 2, a post 5 is installed standing upwards. On the post 5, a jaw rest 6 where the jaw of a patient is to be rested and an external fixation lamp 7 as a light source for fixing an eye E are provided.

On the platform 3, a main body part 8 is installed to accommodate various optical systems or control systems of the fundus camera 1000. Furthermore, the control system may be installed inside the base 2 or the platform 3, etc., or in an external device such as a computer, etc. connected to the fundus camera 1000.

On the side of the eye E of the main body part 8 (the left side of the page in FIG. 11), an objective lens part 8a disposed opposite the eye E is installed. Also, on the examiner's side of the main body part 8 (the right side of the page in FIG. 11), an objective lens part 8b for observing the fundus oculi of the eye E with the naked is installed.

Furthermore, connected to the main body part 8 is a still camera 9 for producing a still image of a fundus oculi of the eye E and an imaging device 10 such as a TV camera, etc. for producing still images or moving images of a fundus oculi. The still camera 9 and the imaging device 10 are formed removably with respect to the main body part 8.

As a still camera 9, in accordance with various conditions such as the purpose of an examination or the saving method of produced images, etc., a digital camera equipped with imaging elements such as CCD (Charge Coupled Device) or CMOS (Complementary Metal Oxide Semiconductor), a film camera, and an instant camera, etc. may interchangeably be used when it is appropriate. The main body part 8 is equipped with a mounting part 8c for interchangeably mounting such a still camera 9.

If the still camera 9 or the imaging device 10 is for taking digital images, the image data of the produced fundus image may be sent to a device such as a computer, etc. connected to the fundus camera 1000 and be observed as a fundus image by being displayed on the display. Also, the image data can be sent to an image storing device connected to the fundus camera 1000 to compile a database and be used as electronic data for creating medical charts, etc.

Furthermore, on the examiner's side of the main body part 8, a touch panel monitor 11 is installed. On this touch panel monitor 11, fundus images of the eye E created based on the video signals output from the still camera 9 (a digital method thereof) or the imaging device 10 are displayed. Moreover, on the touch panel monitor 11, the 2-dimensional coordinate system with the center of the screen as the origin is displayed overlapped with a fundus image. When the screen is touched by the examiner, the coordinate value corresponding to the touched position is displayed.

Next, referring to FIG. 12, a composition of an optical system of the fundus camera 1000 is described. The fundus camera 1000 is provided with an illuminating optical system 100 to light the fundus oculi Ef of an eye E, an imaging optical system 120 to guide the fundus reflection light of the illumination light to the eyepiece part 8b, a still camera 9, and an imaging device 10.

The illuminating optical system 100 comprises: an observation light source 101, a condenser lens 102, an imaging light source 103, a condenser lens 104, an exciter filter 105 and 106, a ring transparent plate 107, a mirror 108, a liquid crystal display (LCD) 109, an illumination diaphragm 110, a relay lens 111, an aperture mirror 112, and an objective lens 113.

The observation light source 101 consists of a halogen lamp, etc. and emits continuous light for observing the fundus. The condenser lens 102 is an optical element that converges the continuous light (observation illumination light) emitted by the observation light source 101 and substantially evenly irradiates the observation illumination light to the fundus oculi.

The imaging light source 103 consists of a xenon lamp, etc. to be flashed when producing fundus oculi Ef images. The condenser lens 104 is an optical element that converges the flash light (imaging illumination light) emitted by the imaging light source 103 and irradiates the fundus oculi Ef evenly with the imaging illumination light.

The exciter filters 105 and 106 are the filters to be used when fluorography of images of a fundus oculi Ef takes a place. The exciter filters 105 and 106 respectively can be inserted and removed on the optical path by a drive mechanism such as a solenoid, etc. The exciter filter 105 is disposed on the optical path in the event of FAG (fluorescein angiography). Whereas, the exciter filter 106 is disposed on the optical path in the event of ICG (indocyanine green angiography). Furthermore, when color images are being obtained, both exciter filters 105 and 106 are retracted from the optical path.

The ring transparent plate 107 is disposed in a conjugating location with a pupil of the eye E, and is equipped with a ring transparent part 107a taking an optical axis of the illuminating optical system 100 as a center. The mirror 108 reflects the illumination light emitted by the observation light source 101 or by the imaging light source 103 in the direction of the optical axis of the imaging optical system 120. The LCD 109 displays a fixation target (not illustrated) for fixing the eye E.

The illumination diaphragm 110 is a diaphragm member to shut out a part of the illumination light for flare prevention, etc. This illumination diaphragm 110 is composed movably in the light axial direction of the illuminating optical system 100, and is thus capable of changing the illuminating region of the fundus oculi Ef.

The aperture mirror 112 is an optical element to combine an optical axis of the illuminating optical system 100 and an optical axis of the imaging optical system 120. In the center region of the aperture mirror 112 an aperture part 112a is opened. The light axis of the illuminating optical system 100 and the light axis of the imaging optical system 120 are to be crossed at a substantially central location of this aperture part 112*a*. The objective lens 113 is installed in the objective lens part 8*a* of the main body part 8.

The illuminating optical system 100 having such a composition illuminates a fundus oculi Ef in the following manner. First, the observation illumination light is emitted when the observation light source 101 is lit during fundus observation. This observation illumination light irradiates the ring transparent plate 107 through the condenser lenses 102 and 104. (The exciter filters 105 and 106 are removed from the optical path.) The light passed through the ring transparent part 107*a* of the ring transparent plate 107 is reflected by the mirror 108 and is reflected along the optical axial direction of the imaging optical system 120 due to the aperture mirror 112 through the LCD 109, the illumination diaphragm 110 and the relay lens 111. The observing illumination light reflected by the aperture mirror 112 advances in the optical axial direction of the imaging optical system 120 and is converged by the objective lens 113, to be made incident onto the eye E, and illuminates the fundus oculi Ef.

Then, the ring transparent plate 107 is disposed in a conjugating location with the pupil of the eye E, and on the pupil a ring shaped image of the entering observation illumination light is formed. The fundus reflection light of the entered observation illumination light is to be emitted from the eye E through a central dark part of the ring image on the pupil. As described, it is to protect the effect of observing illumination light entering the eye E with respect to the fundus reflection light of the observing illumination light.

On the other hand, when imaging the fundus oculi Ef, flush light is emitted from the imaging light source 103 and the imaging illumination light is irradiated onto the fundus oculi Ef through the same path. In the event of photofluographing, either the exciter filter 105 or the exciter filter 106 is disposed selectively on the optical path depending on whether FAG imaging or ICG imaging is carried out.

Whereas, imaging optical system 120 comprises: an objective lens 113, an aperture mirror 112 (an aperture part 112*a* thereof), an imaging diaphragm 121, a barrier filter 122 and 123, a variable magnifying lens 124, a relay lens 125, an imaging lens 126, a quick return mirror 127 and an imaging media 9*a*. Herein, the imaging media 9*a* is an arbitrary imaging media (image pick-up elements such as CCD, camera film, instant film, etc.) used for a still camera 9.

The fundus reflection light of the illumination light, emitted through the central dark part of the ring shaped image formed on the pupil from the eye E, enters the imaging diaphragm 121 through the aperture part 112*a* of the aperture mirror 112. The aperture mirror 112 reflects cornea reflection light of the illumination light and acts so as not to mix the cornea reflection light into the fundus reflection light made incident onto the imaging diaphragm 121. As a result, the generation of flare on the observation images and/or produced images is prevented.

The imaging diaphragm 121 is a plate shaped member at which plural circular light transparent parts of different sizes are formed. The plural light transparent parts constitute different diaphragms with different diaphragm values (F value), and are to be disposed alternatively on the optical path by a drive mechanism (not illustrated herein).

The barrier filters 122 and 123 can be inserted and removed on the optical path by a drive mechanism such as a solenoid, etc. In the event of FAG imaging, the barrier filter 122 is disposed on the optical path while in the event of ICG imaging the barrier filter 123 is inserted onto the optical path. Furthermore, when producing color images the barrier filters 122 and 123 are to be retracted from the optical path.

The variable magnifying lens 124 is to be movable in the light axial direction of the imaging optical system 120 by a drive mechanism (not illustrated herein). This makes it possible to change the magnifying ratio of an observation and the magnifying ratio in imaging, and to focus images of a fundus oculi. The imaging lens 126 is a lens to focus the fundus reflection light from an eye E on the imaging media 9*a*.

The quick return mirror 127 is disposed rotatably around a rotary shaft 127*a* by a drive mechanism not illustrated herein. In the event of imaging a fundus oculi Ef with the still camera 9, the fundus reflection light is supposed to be guided to the imaging media 9*a* by springing up the quick return mirror 127 that is obliquely mounted on the optical path. Whereas, in the event of imaging a fundus oculi with an imaging device 10 or of observing the fundus oculi with the naked eye of the examiner, the quick return mirror 127 is to be obliquely mounted on the optical path to upwardly reflect the fundus reflection light.

The imaging optical system 120 is further provided, for guiding the fundus reflection light reflected by the quick return mirror 127, with a field lens 128, a switching mirror 129, an eyepiece 130, a relay lens 131, a reflection mirror 132, an imaging lens 133 and an image pick up element 10*a*. The image pick up element 10*a* is an image pick up element such as CCD, etc. installed internally in the imaging device 10. On the touch panel monitor 11 a fundus oculi image Ef' imaged by the image pick up element 10*a* is be displayed.

The switching mirror 129 is to be rotatable around the rotary shaft 129*a* as well as the quick return mirror 127. This switching mirror 129 is obliquely disposed on the optical path during observation with the naked eye and guides reflected light on the fundus oculi to the eyepiece 130.

Also, when a fundus image is formed by the imaging device 10, the switching mirror 129 is retracted from the optical path, and the fundus reflection light is guided toward an image pick-up element 10*a*. In this case, the fundus reflection light is directed toward a relay lens 131, is reflected by the mirror 132, and is focused on the image pick-up element 10*a* by the imaging lens 133.

Such a fundus camera 1000 is a fundus observation device to be used for observing the state of the surface of a fundus oculi Ef, that is, the retina. In other words, a fundus camera 1000 is a fundus observation device to obtain a 2-dimensional fundus oculi image when it sees the fundus oculi Ef from the corneal direction onto the eye E. On the other hand, in the deep layer of retina tissues such as the choroidea or sclera exist, technology for observing these deep layer tissues has been desired, but, in recent years, devices for observing these deep layer tissues have been practically implemented (e.g. JP Patent laid-open No. 2003-00543, JP Patent laid-open No. 2005-241464).

The fundus observation device disclosed in JP Patent laid-open No. 2003-00543 and JP Patent laid-open No. 2005-241464 are devices to which so called OCT (Optical Coherence Tomography) technology is applied. With such fundus observation devices, low coherence light is split into two, one of which (signal light) is guided to a fundus oculi and the other one (reference light) is guided to a given reference object, and this is a device to form tomographic images of the surface and the deep layer tissue of a fundus oculi, and to form the 3-dimensional image from the tomographic images, by detecting and analyzing the interference light obtained by overlaying the signal light that has reached the fundus oculi and the reference light that has been reflected by the reference object. Such devices are in general called a Fourier domain OCT.

The Fourier domain OCT is designed to form a tomographic image having a depth-wise cross-section along its scanning line by scanning and irradiating a signal light onto the fundus oculi. Such scanning of signal lights is referred to as a B-scan (see NEDO Workshop "Seeing (examining) inside the body from the 'window' of the human body, the fundus oculi"—Development of an ultra early diagnostic device for lifestyle-related diseases using the latest optical technologies (held on Apr. 25, 2005).

When forming a 3-dimensional image, a B-scan is performed along a plurality of scanning lines, and an interpolation process is applied to the resulting plurality of tomographic images for the generation of 3-dimensional image data. This 3-dimensional image data is referred to as volume data, voxel data, and so forth, as well as medical imaging diagnosis devices such as an X-ray CT device, which is image data in a form in which pixel data (such as luminance value and RGB value regarding brightness, contrasting density and color) is assigned to each voxel. A 3-dimensional image is displayed as a pseudo 3-dimensional image seen from a certain viewing angle obtained by rendering volume data.

When scanning the peripheral region of a fundus oculi with signal light by an optical image measuring device, shading of signal light due to the iris of the eye or the like may occur and thereby the quality of the image may deteriorate, and at worst, an image may not be captured. Therefore, it is preferable to bring the region to be image-captured close to the optical axis of the optical system when capturing an image of the peripheral region of a fundus oculi, so as to avoid shading of signal light.

For that purpose, it is possible to project a fixation target onto the eye and to change the viewing angle of the eye so that the region to be image-captured is arranged close to the optical axis of the optical system. In this case, the relative position of the fundus oculi region to the scanning position of the signal light will be changed.

However, it is not easy to fixate the eye such that the desired position on the fundus oculi is arranged close to the optical axis of the optical system. Consequently, it is not easy to capture an image at the desired position on the fundus oculi.

The present invention is intended to solve the abovementioned problems, with the purpose of providing a fundus observation device capable of easily capturing an image at the desired position on a fundus oculi.

SUMMARY OF THE INVENTION

In order to achieve the above purpose, the first aspect of the present invention is constructed as follows; A fundus observation device comprising: fixation target projecting part including fixation target displaying part and a projection optical system, the fixation target displaying part being configured to display a fixation target for fixating an eye, the projection optical system being configured to project the displayed fixation target onto the a fundus oculi, projection position changing part configured to change the display position of said fixation target so as to change the projection position of the fixation target on the fundus oculi, and image forming part configured to form an image of the fundus oculi with said fixation target projected based on optically captured data, wherein s aid image forming part forms a 2-dimensional image of the surface of a fundus oculi based on optically captured data and further comprises displaying part configured to display the formed 2-dimensional image, and said projection position changing part includes operation part configured to specify a position on said displayed 2-dimensional image and changes the display position of said fixation target based on the position specified by said operation part.

BRIEF DESCRIPTION OF THE DRAWINGS

FIG. 8 is a schematic diagram representing one example of scanning features of signal light in a preferred embodiment of the fundus observation device related to the present invention.

DETAILED DESCRIPTION OF THE REFERENCE EMBODIMENTS

Figure 11:
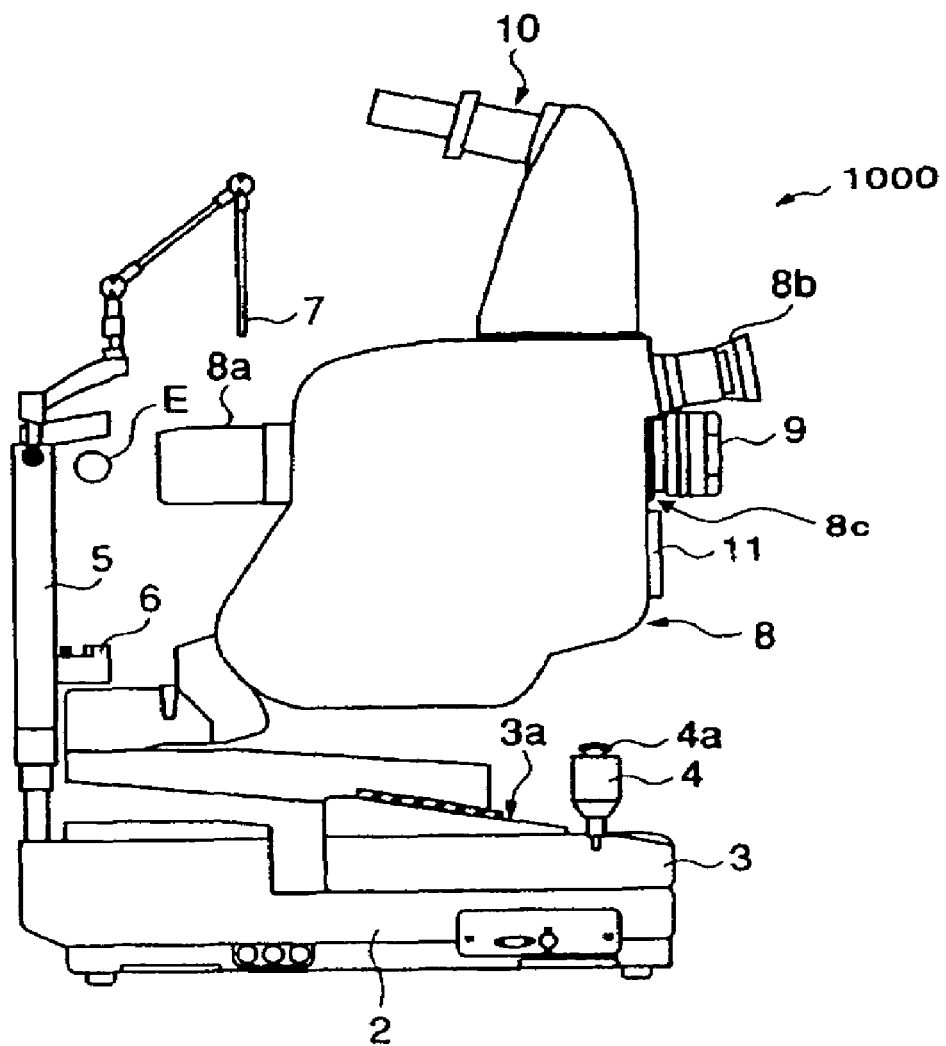
FIG. 11 is a schematic diagram showing one example of the appearance of a tomographic image of the fundus oculi acquired with a conventional fundus observation device (optical image measuring device).
Figure 12:
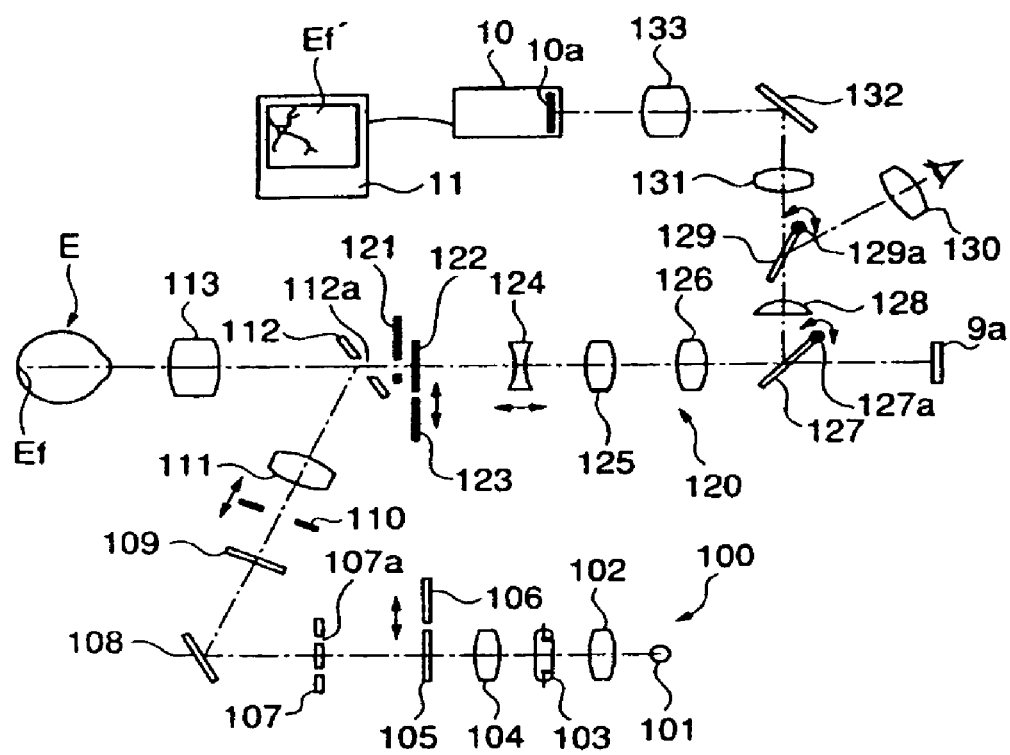
FIG. 12 is a schematic diagram representing one example of an internal configuration (an optical system configuration) of a conventional fundus observation device (fundus camera).

One example of favorable embodiments of a fundus observation device related to the present invention is described in detail referring to figures. Furthermore, for structual parts that are the same as conventional ones, the same symbols used in FIG. 11 and FIG. 12 are used.

Figure 1:
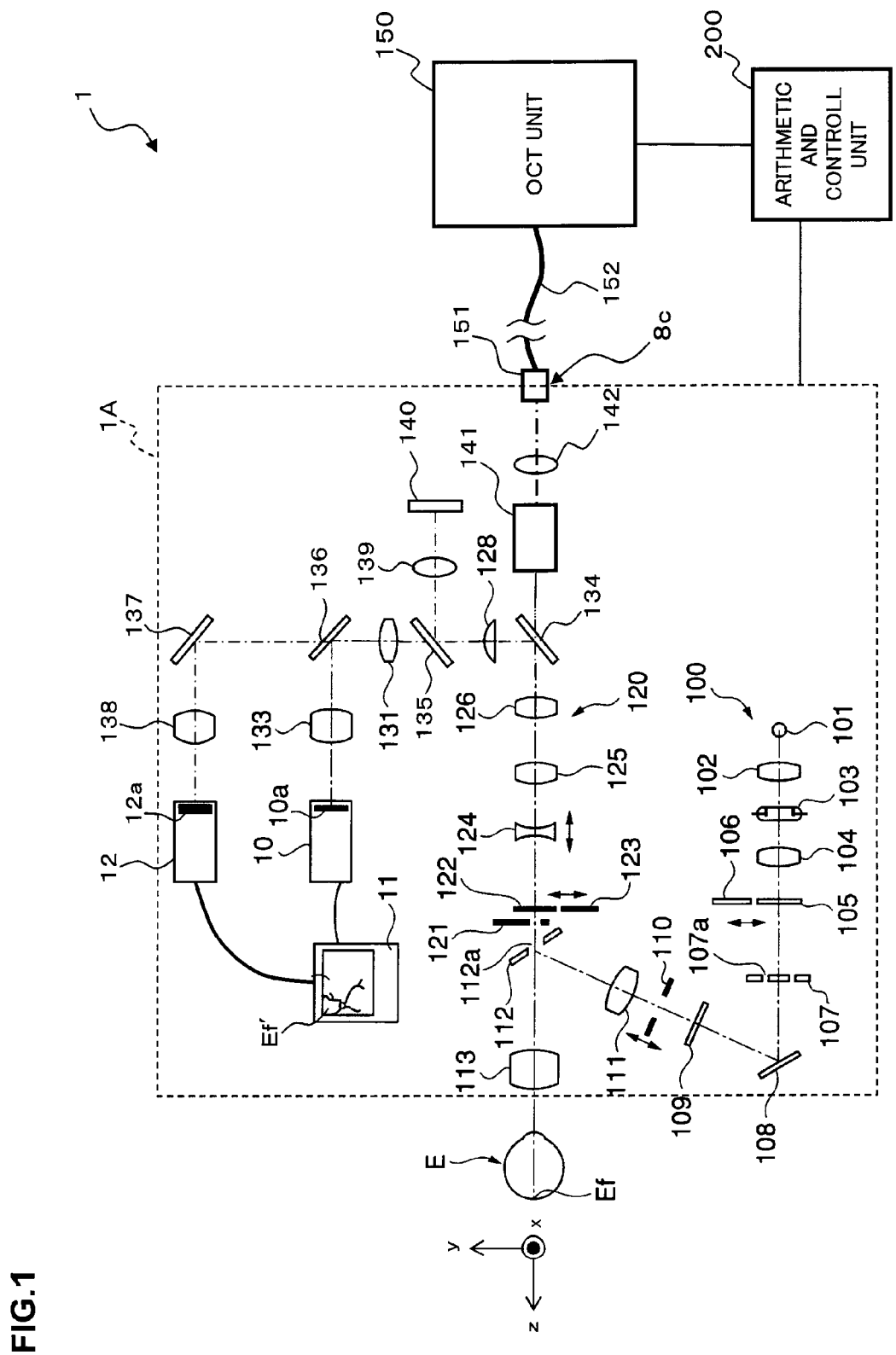
FIG. 1 is a schematic diagram representing one example of the entire structure in a preferred embodiment of the fundus observation device related to the present invention.
Figure 2:
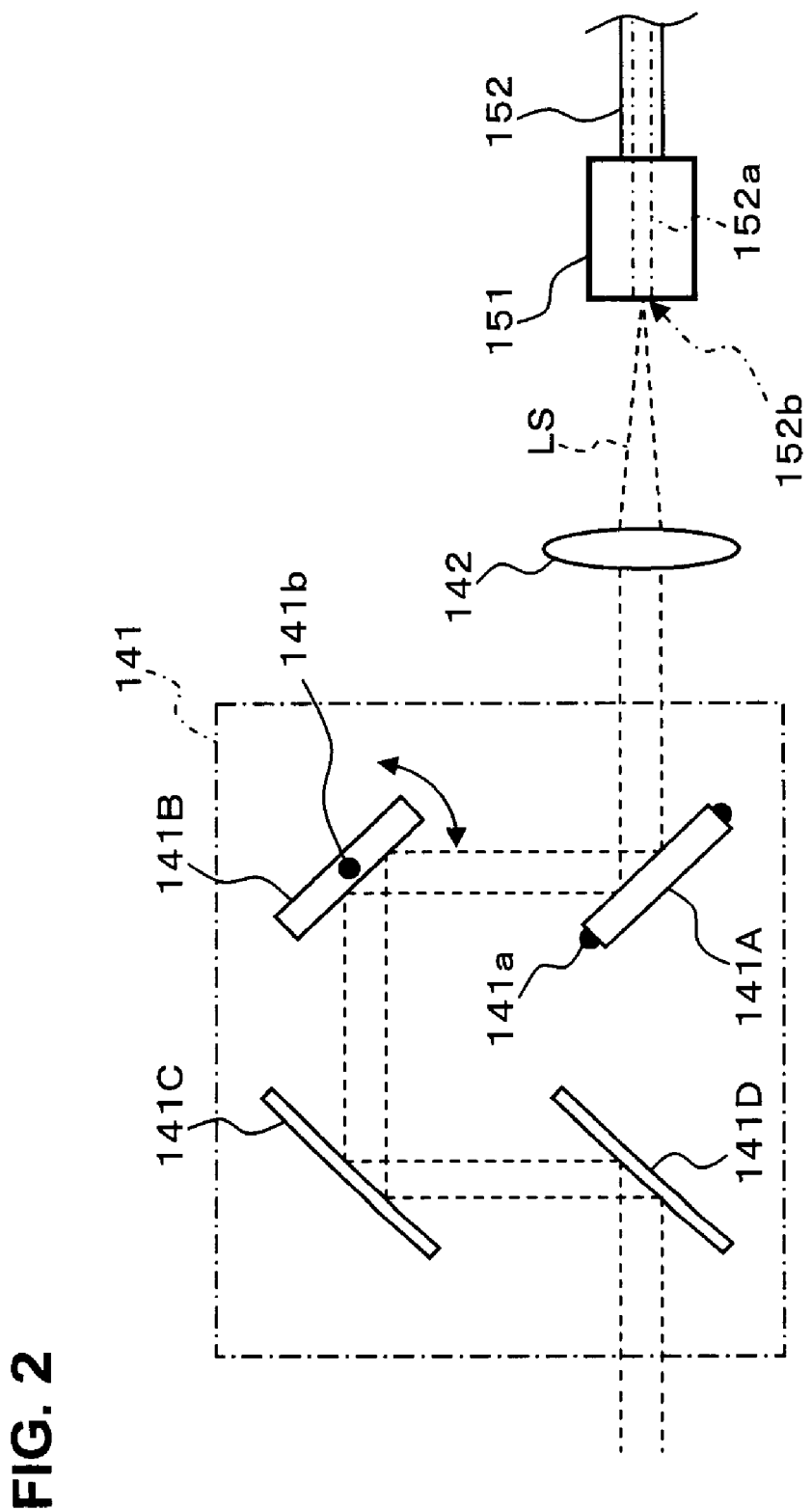
FIG. 2 is a schematic diagram representing one structural example of a scanning unit installed in a fundus camera unit in a preferred embodiment of the fundus observation device related to the present invention.
Figure 3:
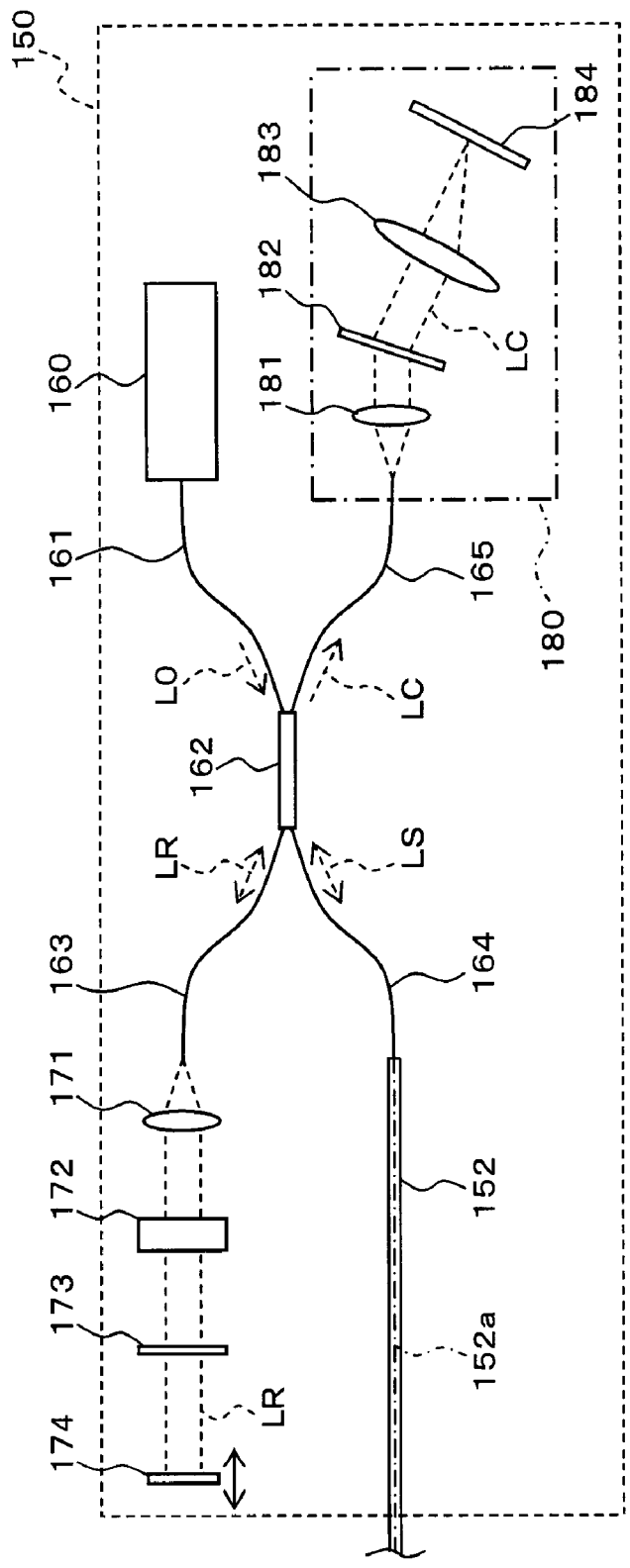
FIG. 3 is a schematic diagram representing one structural example of an OCT unit in a preferred embodiment of the fundus observation device related to the present invention.
Figure 4:
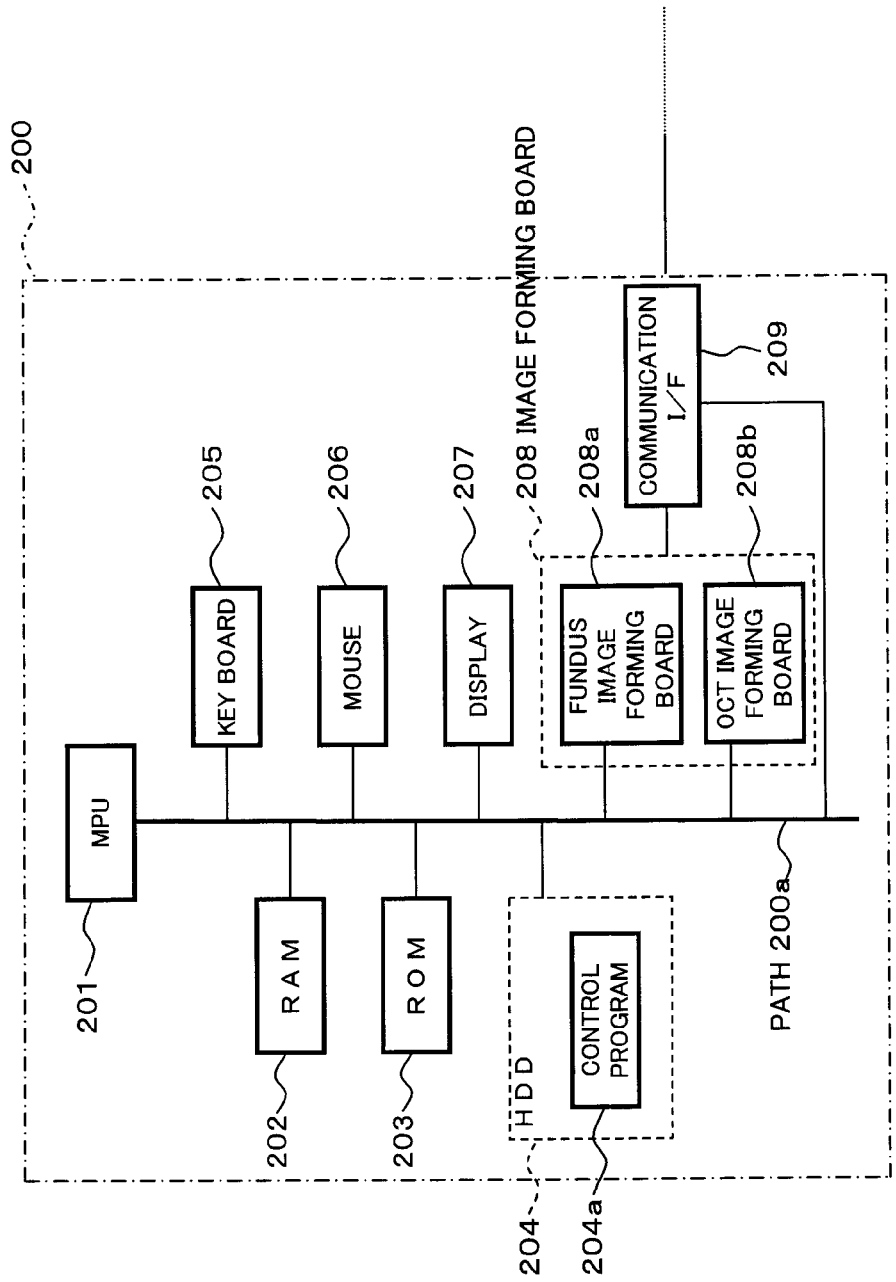
FIG. 4 is a schematic block diagram representing one example of hardware configurations of an arithmetic and control unit in an embodiment of the fundus observation device related to the present invention.
Figure 5:
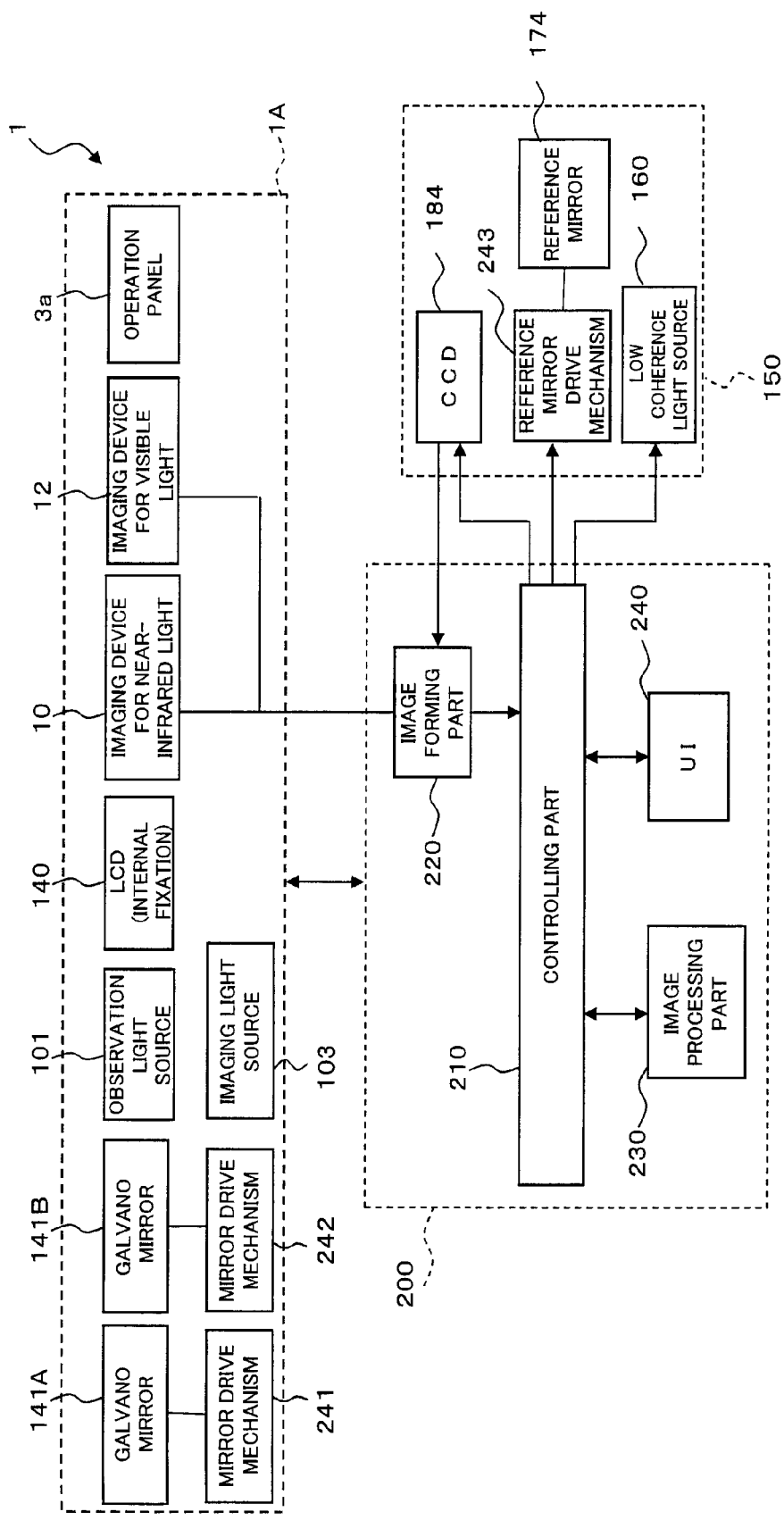
FIG. 5 is a schematic block diagram representing one structural example of a control system in a preferred embodiment of the fundus observation device related to the present invention.
Figure 6:
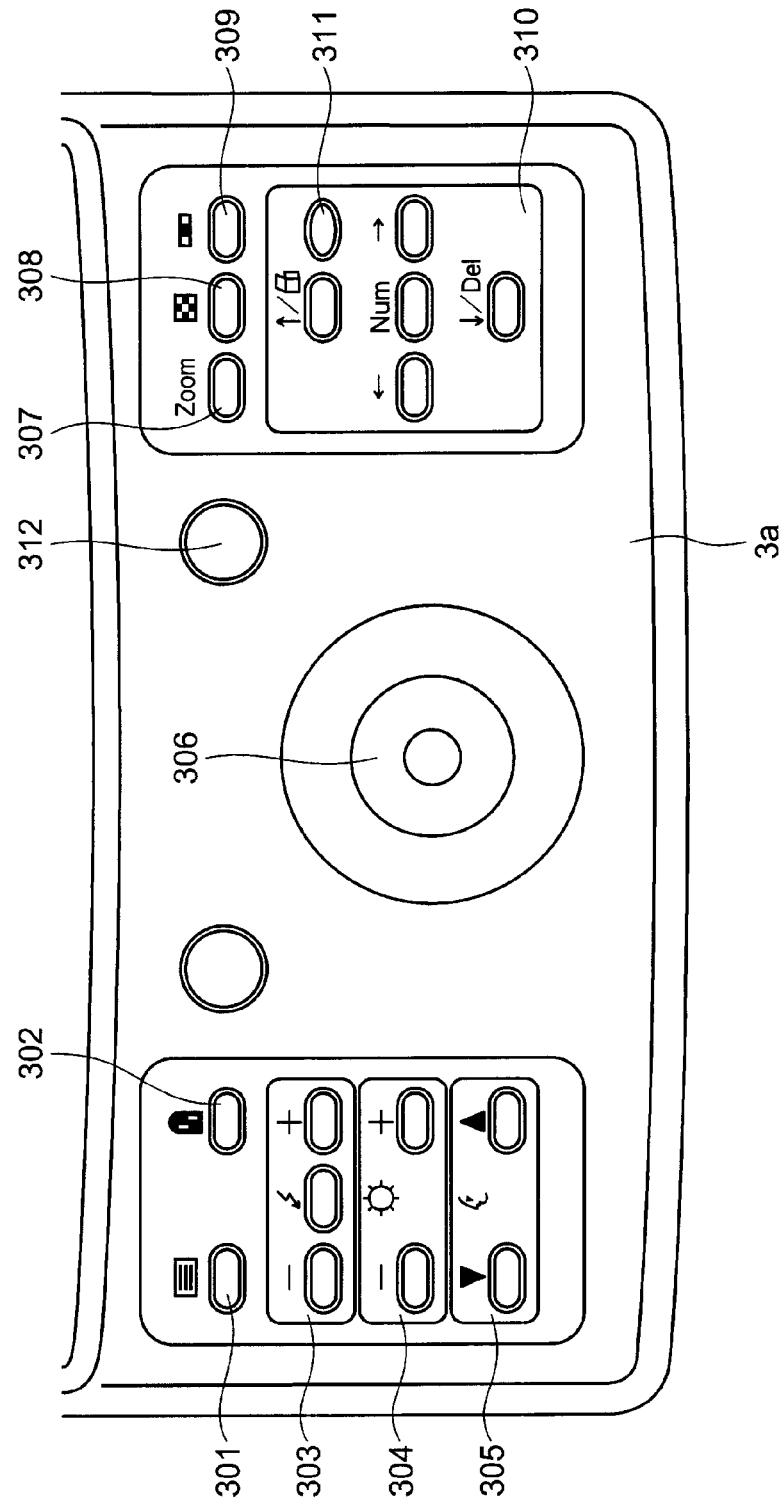
FIG. 6 is a schematic diagram showing an example of the apparent configuration of the operation panel in a preferred embodiment of the fundus observation device related to the present invention.
Figure 7:
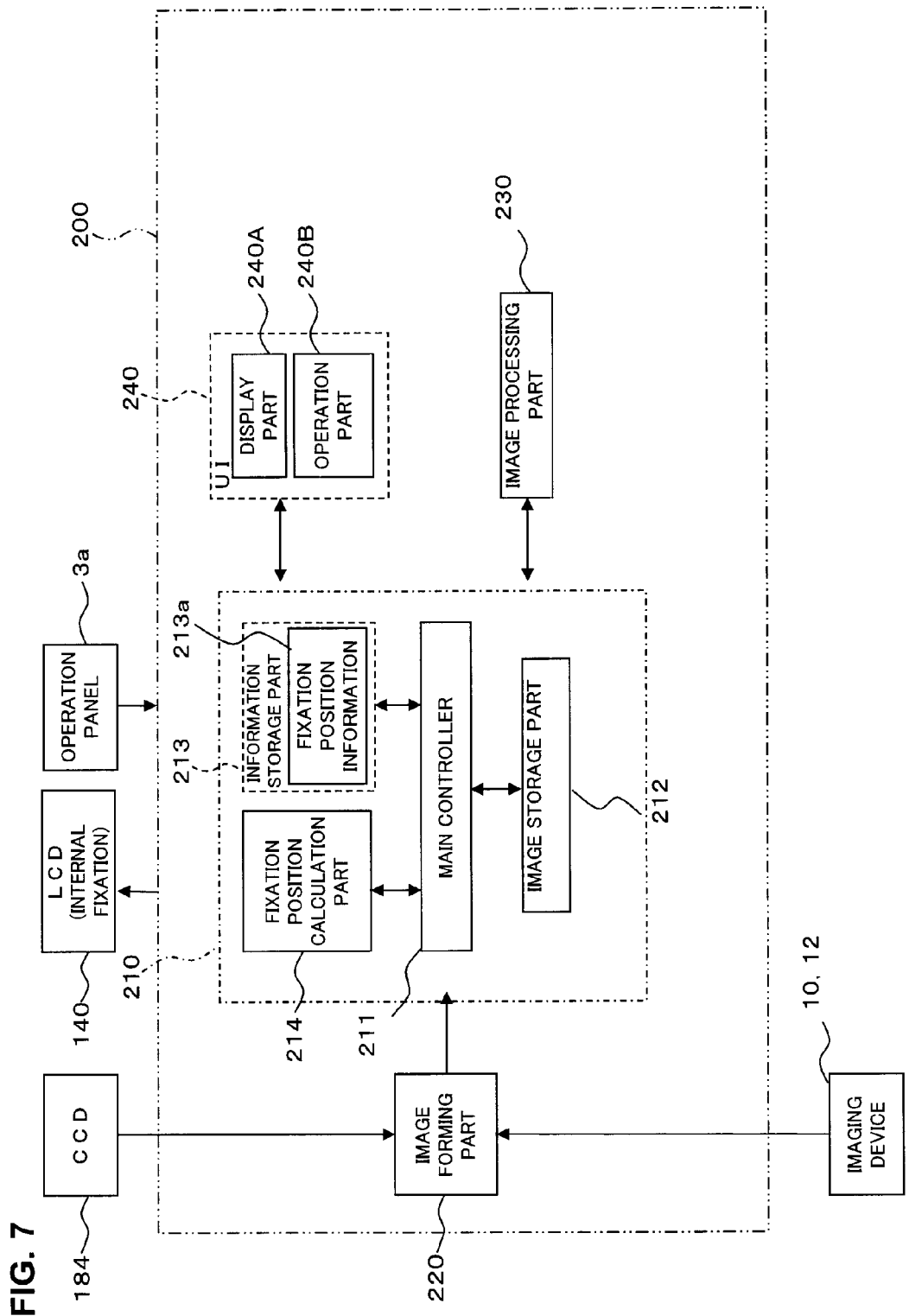
FIG. 7 is a drawing showing a structural example of the arithmetic and control unit in an preferred embodiment related to the present invention.

First, by referring to FIGS. 1 through 7, the constitution of the fundus observation device related to the present invention is described. FIG. 1 shows the entire constitution of the fundus observation device 1 related to the present invention. FIG. 2 shows a constitution of a scanning unit 141 in a fundus camera unit 1A. FIG. 3 shows a constitution of an OCT unit 150. FIG. 4 shows a hardware configuration of an arithmetic and control unit 200. FIG. 5 shows a configuration of a control system of the fundus observation device 1. FIG. 6 shows a constitution of an operation panel 3a provided on a fundus camera unit 1A. FIG. 7 shows a configuration of a control system of an arithmetic and control unit 200.

The Entire Configuration

As shown in FIG. 1, the fundus observation device 1 is comprised of a fundus camera unit 1A that functions as a fundus camera, an OCT unit 150 accommodating the optical system of an optical image measuring device (OCT device), and an arithmetic and control unit 200 that executes various arithmetic processes and control processes, etc.

To the OCT unit 150, one end of a connection line 152 is attached. To the other end of this connection line 152, a connector part 151 is attached. This connector part 151 is attached to a mounting part 8c shown in FIG. 11. Furthermore, a conductive optical fiber runs through the inside of the connection line 152. The OCT unit 150 and the fundus camera unit 1A are optically connected through the connection line 152. The constitution details of the OCT unit 150 are to be described later referring to FIG. 3.

Configuration of Fundus Camera Unit

A fundus camera unit 1A is a device for forming a 2-dimensional image of the surface of a fundus oculi of an eye based on optically captured data (data detected by imaging devices 10 and 12), and the fundus camera unit 1A has substantially the same appearance as the conventional fundus camera 1000 shown in FIG. 11. Furthermore, as in the conventional optical system shown in FIG. 12, the fundus camera unit 1A is provided with an illuminating optical system 100 to light a fundus oculi Ef of an eye E, and an imaging optical system 120 for guiding the fundus reflection light of the illumination light to an imaging device 10.

In addition, although the details are to be described later, an imaging device 10 in an imaging optical system 120 of the present embodiment is used for detecting the illumination light with a wavelength in the near-infrared region. Furthermore, in this imaging optical system 120, an imaging device 12 for detecting the illumination light with a wavelength in the visible region is provided separately. In addition, in this imaging optical system 120, it can guide the signal light from the OCT unit 150 to the fundus oculi Ef and the signal light through the fundus oculi Ef to the OCT unit 150.

Also, the illuminating optical system 100 is comprised as in conventional ones including: an observation light source 101, a condenser lens 102, an imaging light source 103, a condenser lens 104, an exciter filter 105 and 106, a ring transparent plate 107, a mirror 108, an LCD 109, an illumination diaphragm 110, a relay lens 111, an aperture mirror 112, and an objective lens 113.

The observation light source 101 emits the illumination light of a wavelength in the visible region included within about 400 nm to 700 nm. Furthermore, the imaging light source 103 outputs the illumination light of a wavelength in the near-infrared region included within about 700 nm to 800 nm. The near-infrared light output from this imaging light source 103 is provided shorter than the wavelength of the light used by the OCT unit 150 (to be described later).

The imaging optical system 120 comprises: an objective lens 113, an aperture mirror 112 (aperture part 112a thereof), an imaging diaphragm 121, a barrier filter 122 and 123, a variable magnifying lens 124, a relay lens 125, an imaging lens 126, a dichroic mirror 134, a field lens 128, a half mirror 135, a relay lens 131, a dichroic mirror 136, an imaging lens 133, an imaging device 10 (an image pick-up element 10a), a reflection mirror 137, an imaging lens 138, an imaging device 12 (an image pick-up element 12a), and a lens 139 and LCD (Liquid Crystal Display) 140.

The imaging optical system 120 related to the present embodiment is different from the conventional imaging optical system 120 shown in FIG. 12 in that the dichroic mirror 134, the half mirror 135, a dichroic mirror 136, the reflection mirror 137, the imaging lens 138, and the lens 139 and LCD 140 are provided.

The dichroic mirror 134 reflects the fundus reflection light of the illumination light (with a wavelength included within about 400 nm to 800 nm) from the illuminating optical system 100, and transmits the signal light LS (with a wavelength included within about 800 nm to 900 nm; to be described later) from the OCT unit 150.

Furthermore, the dichroic mirror 136 transmits the illumination light with a wavelength in the visible region from the illuminating optical system 100 (the visible light of a wavelength within about 400 nm to 700 nm emitted from the observation light source 101) and reflects the illumination lights having a wavelength in the near-infrared region (near-infrared light of a wavelength within about 400 nm to 700 nm emitted from the observation light source 101).

The LCD 140 shows an internal fixation target, etc. The light from this LCD 140 is reflected by the half mirror 135 after being converged by the lens 139, and is reflected by the dichroic mirror 136 through the field lens 128. Further, it enters the eye E passing through the imaging lens 126, the relay lens 125, the variable magnifying lens 124, the aperture mirror 112 (aperture part 112a thereof), the objective lens 113, etc. As a result, an internal fixation target, etc. is displayed in a fundus oculi Ef of an eye E.

The image pick up element 10a is the image pick up element of CCD and CMOS, etc. installed internally in an imaging device 10 such as a TV camera, and is particularly used for detecting light of a wavelength in the near-infrared region (that is, the imaging device 10 is the infrared TV camera for detecting near-infrared light). The imaging device 10 outputs the video signal as a result of detecting near-infrared light. A touch panel monitor 11 displays a 2-dimensional image (fundus image Ef') of the surface of the fundus oculi Ef based on this video signal. Also, this video signal is sent to the arithmetic and control unit 200, and the fundus oculi image is displayed on the display (to be described later). Furthermore, when the fundus oculi are being imaged by this imaging device 10, for example, the illumination light emitted from the imaging light source 103 of the illuminating optical system 100, having a wavelength in the near-infrared region, may be used.

Also, the image pick up element 12a is the image pick up element of CCD and CMOS, etc. installed internally in an imaging device 12 such as a TV camera, and is particularly used for detecting light of a wavelength in the visible region (that is, the imaging device 12 is the TV camera for detecting visible light). The imaging device 12 outputs the video signal as a result of detecting visible light. A touch panel monitor 11 displays a 2-dimensional image (fundus image Ef') of the surface of the fundus oculi Ef based on this video signal. Also, this video signal is sent to the arithmetic and control unit 200, and the fundus oculi image is displayed on the display (to be described later). Furthermore, when the fundus oculi are being imaged by this imaging device 12, for example, the illumination light emitted from the observation light source 101 of the illuminating optical system 100, having a wavelength in the visible region, may be used.

Furthermore, the imaging optical system 120 of the present embodiment is provided with a scanning unit 141 and a lens 142. The scanning unit 141 is equipped with a constitution to scan the light (signal light LS; to be described later) emitted from the OCT unit 150 on a fundus oculi Ef.

The lens 142 incidents the signal light LS from the OCT unit 150 in the form of parallel light flux onto the scanning unit 141. Furthermore, the lens 142 acts so as to converge the fundus reflection light of the signal light LS that has reached through the scanning unit 141.

In FIG. 2, one example of a concrete constitution of the scanning unit 141 is shown. The scanning unit 141 is comprised including Galvano mirrors 141A, 141B, and reflection mirrors 141C, 141D.

The Galvano mirrors 141A and 141B are to be rotatable centering around rotary shafts 141a and 141b respectively. The rotary shaft 141a and 141b are arranged perpendicular to each other. In FIG. 2, the rotary shaft 141a of the Galvano mirror 141A is arranged parallel to the paper face, while the rotary shaft 141b of the Galvano mirror 141B is arranged perpendicular to the paper face. That is, the Galvano mirror 141B is to be rotatable in the directions indicated by an arrow pointing in both directions in FIG. 2, while the Galvano mirror 141A is to be rotatable in the directions perpendicular to the arrow pointing in both directions. As a result, this pair of Galvano mirrors 141A and 141B act so that the reflecting direction of the signal light LS changes to a direction perpendicular to each other. Furthermore, the rotary movement of the Galvano mirror 141A and 141B respectively is driven by a drive mechanism (see FIG. 5) to be described later.

The signal light LS reflected by the Galvano mirrors 141A and 141B is to be reflected by reflection mirrors 141C and 141D, and is to advance in the same direction as having entered into the Galvano mirror 141A.

As described previously, a conductive optical fiber 152a runs inside the connection line 152, and the end face 152b of the optical fiber 152a is arranged opposing the lens 142. The signal light LS emitted from this end face 152b advances while gradually expanding its beam diameter toward the lens 142 until being converged to a parallel light flux by this lens 142. On the contrary, the fundus reflection light of the signal light LS is converged toward the end face 152b by this lens 142.

Configuration of OCT Unit

Next, the configuration of an OCT unit 150 is described with reference to FIG. 3.

The OCT unit 150 shown in the FIG. 3 is a device for forming a tomographic image of fundus oculi based on data captured by an optical scan (data detected by CCD 184 to be described below). The OCT unit 150 has a similar optical system to a conventional optical image measuring device. That is, the OCT unit 150 has an interferometer that splits the light emitted from a light source into a reference light and a signal light, and generates interference light by superposing the reference light having reached the reference object and the signal light having reached the object to be measured (fundus oculi Ef), and a device configured to output a signal as a result of detecting the interference light toward the arithmetic and control unit 200. The arithmetic and control unit 200 forms an image of the object to be measured (fundus oculi Ef) by analyzing this signal.

A low coherence light source 160 is composed of a broad band light source such as super luminescent diode (SLD) or a light emitting diode (LED), etc that emits low coherence light L0. This low coherence light L0, for instance, has a wave length in the near-infrared region and is supposed to be light having a time wise coherence length of approximately several tens of micro-meters. The low coherence light LO emitted from the low coherence light source 160 has a longer wavelength than the illumination light (wavelength: about 400 nm to 800 nm) of the fundus camera unit 1A, for example, a wavelength included within about 800 nm to 900 nm.

The low coherence light L0 emitted from the low coherence light source 160 is guided to an optical coupler 162 through an optical fiber 161 composed of, e.g. a single mode fiber, or PM (Polarization maintaining) fiber, and then split into reference light LR and signal light LS.

Furthermore, the optical coupler 162 has both actions, i.e. a device for splitting lights (splitter), and a device for superposing lights (coupler); however, herein conventionally referred to as an "optical coupler".

The reference light LR generated by the optical coupler 162 is guided by an optical fiber 163 consisting of such as a single mode fiber, and emitted from the end face of the fiber. The emitted reference light LR is reflected by a reference mirror 174 (reference object) through a glass block 172 and a density filter 173 after having been converged into a parallel light flux by a collimator lens 171.

The reference light LR reflected by the reference mirror 174 is converged to the end face of the optical fiber 163 by the collimator lens 171 again through the density filter 173 and the glass block 172. The converged reference light LR is guided to the optical coupler 162 through the optical fiber 163.

Furthermore, the glass block 172 and the density filter 173 act as a delaying a device for matching the optical path length (optical distance) between the reference light LR and the signal light LS, and as a device for matching the dispersion characteristics of reference light LR and the signal light LS.

Furthermore, the reference mirror 174 is provided to be movable in the propagating direction of the reference light LR. As a result, it ensures the light path length of the reference light LR according to the axial length, etc. of an eye E. Moreover, the reference mirror 174 is operated to move by a drive mechanism including a motor, etc.

Whereas, the signal light LS generated by the optical coupler 162 is guided to the end part of the connection line 152 by an optical fiber 164 consisting of such as a single mode fiber. A conductive optical fiber 152a runs inside the connection line 152. Herein, the optical fiber 164 and the optical fiber 152a may be composed of a single optical fiber, or may be jointly formed by connecting each end. In either case, it is sufficient as long as the optical fiber 164 and 152a are composed so as to be capable of transferring the signal light LS between the fundus camera unit 1A and the OCT unit 150.

The signal light LS is guided within the connection line 152 to the fundus camera unit 1A. Then, the signal light LS enters into the eye E through the lens 142, the scanning unit 141, the dichroic mirror 134 the imaging lens 126, the relay lens 125, the variable magnifying lens 124, the imaging diaphragm 121, the aperture part 112a of an aperture mirror 112, and the objective lens 113 (then, the barrier filter 122 and 123 are retracted from the optical path respectively).

The signal light LS that has entered into the eye E forms an image on a fundus oculi (retina) Ef and is then reflected. Then, the signal light LS is not only reflected on the surface of the fundus oculi Ef, but is also scattered at the refractive index boundary reaching the deep area of the fundus oculi Ef. As a result, the signal light LS reached the fundus Ef becomes a light containing the information reflecting the surface state of the fundus oculi Ef and the information reflecting the scattered state in the rear at the refractive index boundary of the deep area tissue. The light is simply referred as "fundus reflection light of the signal light LS.

The fundus reflection light of the signal light LS advances reversely on the above path and converges at the end face 152b of the optical fiber 152a, then enters into the OCT unit 150 through this optical fiber 152a, and returns to the optical coupler 162 through the optical fiber 164. The optical coupler 162 overlays this signal light LS on the reference light LR reflected at the reference mirror 174 to generate interference light LC. The generated interference light LC is guided into a spectrometer 180 through an optical fiber 165 consisting of such as a single mode fiber.

Furthermore, although a Michelson type interferometer has been adopted in the present embodiment, for instance, a Mach Zender type, etc. or any optional type of interferometer may be adopted appropriately.

The spectrometer 180 is comprised of a collimator lens 181, a diffraction grating 182, an image forming lens 183, and a CCD (Charge Coupled Device) 184. The diffraction grating 182 in the present embodiment is a transmission type diffraction grating; however, needless to say, a reflection type diffraction grating may also be used. Furthermore, needless to say, in place of CCD 184, it is also possible to adopt other photo-detecting elements.

The interference light LC entered the spectrometer 180 is to be resolved into spectra by the diffraction grating 182 after having been converged into a parallel light flux by the collimator lens. The split interference light LC forms an image on the image pick up surface of the CCD 184 by the image forming lens 183. The CCD 184 receives this interference light LC that is to be converted to an electrical detection signal, and outputs this detection signal to the arithmetic and control unit 200.

Configuration of Arithmetic and Control Unit

Next, the configuration of the arithmetic and control unit 200 is described. This arithmetic and control unit 200 analyzes the detection signal input from the CCD 184 of the spectrometer 180 of the OCT unit 150, and performs a process of forming tomographic images of a fundus oculi Ef of an eye E. The analysis technique then is the same technique as the conventional Fourier domain OCT technique.

Also, the arithmetic and control unit 200 operates to form (image data of) a 2-dimensional image showing the state of the surface of a fundus oculi Ef (retina) based on the video signal output from the imaging device 10 and 12 of the fundus camera unit 1A.

Furthermore, the arithmetic and control unit 200 executes the control of each part of the fundus camera unit 1A and the control of each part of the OCT unit 150.

As for the control of the fundus camera unit IA, to be controlled is, for example: the emission of illumination light by the observation light source 101 or the imaging light source 103; the insertion/retraction operation of the exciter filters 105, 106, or the barrier filters 122, 123 on the optical path; the display operation of the LCD 140; the shift of the illumination diaphragm 110 (controlling the diaphragm value); the diaphragm value of the imaging diaphragm 121; the shift of the variable magnifying lens 124 (controlling the magnification), etc.

Whereas, as for the control of the OCT unit 150, emission control of the low coherence light by a low coherence light source 160, control of accumulated time of the CCD 184, and movement control of reference mirror 174, etc. are to be performed.

The hardware configuration of the arithmetic and control unit 200 that acts as described above is explained referring to FIG. 4. The arithmetic and control unit 200 is provided with a hardware configuration that is the same as conventional computers. To be specific, the configuration includes: a microprocessor 201 (CPU,MPU, etc.), a RAM202, a ROM203, a hard disk drive (HDD) 204, a key board 205, a mouse 206, a display 207, an image forming board 208, and a communication interface (I/F)209. Each part of these is connected through a bus 200a.

The microprocessor 201 executes operations characteristic to the present embodiment by loading a control program 204a that has been stored in the hard disk drive 204, on the RAM 202.

Furthermore, the microprocessor 201 executes control of each part of the device that has previously been described and various arithmetic processes, etc. Moreover, control of each part of the device that responds to an operation signal from the key board 205 or the mouse 206, control of display processes by the display 207, and control of transmitting/receiving processes of various types of data or control signals, etc. are executed by the communication interface 209.

The key board 205, the mouse 206 and the display 207 are used as a user interface of the fundus observation device 1. The key board 205 is used as a device for inputting letters or figures, etc. by typing. The mouse 206 is used as a device to perform various input operations with respect to the display screen of the display 207.

Furthermore, the display 207 may be any display device such as LCD (Liquid Crystal Display) or CRT (Cathode Ray Tube), etc. which is configured to display images of a fundus oculi Ef formed by the fundus observation device 1 and also configured to display various operation screens or set up screens, etc. This display 207 (and /or a touch panel monitor 11) corresponds to one example of "display part" of the present invention.

Furthermore, the user interface of the fundus observation device 1 is not limited to such a configuration but may be configured by using any user interfaces equipped with a function to display various information and a function to input various information such as track ball, control lever, touch panel type LCD, control panel for ophthalmology examinations.

An image forming board 208 is a dedicated electronic circuit for operating to form (image data of) the image of the fundus oculi Ef of an eye E. In this image forming board 208, the fundus image forming board 208a and OCT image forming board 208b are installed. The fundus image forming board 208a is a dedicated electronic circuit for operating in order to form the image of the fundus oculi Ef based on the video signal from the imaging device 10 or the imaging device 12 of the fundus camera unit 1A. Furthermore, the OCT image forming board 208b is a dedicated electronic circuit for operating in order to form image data of tomographic images of fundus oculi Ef based on the detecting signal from CCD 184 of the spectrometer 180 in the OCT unit 150. The image forming board 208 allows the processing speed for forming image data of fundus images Ef and tomographic images to improve.

A communication interface 209 operates to send the control signal from a microprocessor 201 to the fundus camera unit 1A and OCT unit 150. Also, the communication interface 209 operates to receive the video signal from the imaging device 10 and 12 in the fundus camera unit 1A and the detecting signal from CCD 184 in the OCT unit 150, and it operates to input the signals to the image forming board 208. At this time, the communication interface 209 operates to input the video signal from the imaging device 10 and 12 to the fundus image forming board 208a, and it operates to input the detecting signal from CCD 184 to OCT image forming board 208b.

Moreover, when the arithmetic and control unit 200 is connected to a network such as LAN (Local Area Network) or Internet, etc., the communication interface 209 may be configured to be equipped with a network adopter such as LAN card, etc. or a communication equipment such as modem, etc. so as to be able to perform data communication through the network. In this case, a server accommodating the control program 204a may be installed, and at the same time, the arithmetic and control unit 200 may be configured as a client terminal of the server.

Control System Configuration

The configuration of the control system of the fundus observation device 1 having the configuration described above is explained referring to FIG. 5 and FIG. 7. FIG. 5 shows a part related to the operations or processes of the present embodiment that has been particularly selected from among constituents composing the fundus observation device 1. FIG. 6 shows a constitution of an operation panel 3a provided on a fundus camera unit 1A. FIG. 7 shows a detailed constitution of the arithmetic and control unit 200.

Controlling Part

The control system of the fundus observation device 1 is configured mainly having a controlling part 210 of the arithmetic and control unit 200. The controlling part 210 is comprised including: the microprocessor 201, the RAM202, the ROM203, the hard disk drive 204 (control program 204a), and the communication interface 209.

The controlling part 210 executes said controlling processes by the microprocessor 201 that is operated based on the control program 204a. In particular, the controlling part 210 executes control for allowing the LCD 140 to display an internal fixation target and control of the mirror drive mechanism 241, 242 of the fundus camera unit 1A to independently work the Galvano mirrors 141A, 141B as well as control of the reference mirror drive mechanism 243 to move the reference mirror 174 toward the direction in which the reference light LR travels.

Furthermore, the controlling part 210 executes control for allowing the display 207 of the user interface 240 to display two kinds of images produced by the fundus observation device 1: that is, a 2-dimensional image (fundus image Ef) of the surface of a fundus oculi Ef by the fundus camera unit 1A, and an tomographic image(sectional image, 3-dimensional image, etc.) of a fundus oculi Ef formed based on the detection signal obtained by the OCT unit 150. These images can be displayed on the display 207 both respectively and simultaneously. As to the details of constitution of the controlling part 210, it is described later according to FIG. 7.

Image Forming Part

An image forming part 220 is intended to operate the process forming the fundus image based on the video signal from the imaging device 10 and 12 of the fundus camera unit 1A and to operate the process forming image data of the tomographic images of fundus oculi Ef based on the detecting signal from CCD 184 in the OCT unit 150. This image forming part 220 comprises an imaging forming board 208. In addition, "image" may be identified with corresponding "image data" relating to the present invention.

An image forming part 220 is a configuration of one example of the "image forming part" relating to the present invention with a fundus camera unit 1A and OCT unit 150.

Herein, each part of the fundus camera unit 1A for capturing a 2-dimensional image of the surface of the fundus oculi Ef and the image forming part 220 and explained as one example of the "first image forming part" relating to the present invention. In addition, each part of the fundus camera unit 1A for capturing a tomographic image of the fundus oculi Ef, the OCT unit 150, and the image forming part 220 and explained as one example of the "second image forming part" relating to the present invention.

Image Processing Part

The image processing part 230 is used for various image processes to image data of the images formed by the image forming part 220. For example, it operates to form image data of a 3-dimensional image of the fundus oculi Ef based on the tomographic images of the fundus oculi Ef corresponding to the detection signal from the OCT unit 150 and executes various corrections, such as brightness adjustment.

Herein, 3-dimensional data is image data made by assigning voxel values to each of a plurality of voxels arranged 3-dimensionally, referred to as volume data, voxel data, and so forth. When displaying an image based on volume data, the image processing part 230 operates to form image data of a pseudo 3-dimensional image seen from a particular viewing direction by applying a rendering process (such as volume rendering and MIP (Maximum Intensity Projection)) to this volume data. A display device such as a display device 207 will display such a pseudo 3-dimensional image based on the image data.

User Interface

The user interface (UI) 240, as shown in FIG. 7, comprises a display part 240A consisting of a display device such as a display 207, and an operation part 240B consisting of an operation device and an input device such as a keyboard 205 and mouse 206. The operation part 240B corresponds to one example of "operation part" relating to the present invention.

Operation Panel

The operation panel 3a of the fundus camera unit 1A is described below. This operation panel 3a is, as shown for example in FIG. 11, arranged on the platform 3 of the fundus camera unit 1A. The operation panel 3a in the present embodiment is different from the conventional configuration described above, which is provided with an operation part used to input an operation request for capturing a 2-dimensional image of the surface of the fundus oculi Ef and an operation part used for the input operation of capturing a tomographic image of the fundus oculi Ef (traditionally, only the former operation part). Consequently, the OCT can also be operated in the same manner as operation of a traditional fundus camera.

The operation panel 3a in the present embodiment is, as shown in FIG. 6, provided with a menu switch 301, a split switch 302, an imaging light amount switch 303, an observation light amount switch 304, a jaw holder switch 305, a photographing switch 306, a zoom switch 307, an image switch 308, a fixation target switch 309, a fixation target position adjusting switch 310, a fixation target size switch 311 and a mode switching knob 312.

The menu switch 301 is a switch operated to display a certain menu display for a user to select and specify various types of menus (such as a photographing menu for photographing a 2-dimensional image of the surface of the fundus oculi Ef and a tomographic image of the fundus oculi Ef, and a setting menu for inputting various types of settings). When this menu switch 301 is operated, the operation signal will be input to the controlling part 210. The controlling part 210 displays a menu screen on the touch panel monitor 11 or the display part 240A in response to the input of this operation signal. Incidentally, a controlling part (not shown) may be provided in the fundus camera unit 1A and this controlling part may cause the touch panel monitor 11 to display the menu screen.

The split switch 302 is a switch operated to switch the light on and off of the split bright line for focusing (e.g., see JP Patent laid-open No. H9-66031 or the like. Also referred to as split target, split mark and so on.). Incidentally, the configuration for projecting this split bright line onto an eye E to be examined (split bright line projection part) is housed, for example, in the fundus camera unit 1A (omitted in FIG. 1). When the split switch 302 is operated, the operation signal will be input to the controlling part 210 (or the above controlling part in the fundus camera unit 1A; hereinafter same as this). The controlling part 210 projects the split bright line onto the eye E to be examined by controlling the split bright line projection part in response to the input of this operation signal.

The imaging light amount switch 303 is a switch operated to adjust the emission light amount of the imaging light source 103 (photographing light amount) depending on the state of the eye E to be examined (such as the degree of opacity of the lens). This imaging light amount switch 303 is provided with, for example, a photographing light amount increasing switch "+" for increasing the photographing light amount, a photographing light amount decreasing switch "−", and reset switch (button in the middle) for setting the photographing ling amount to a certain initial value (default value). When one of the imaging light amount switches 303 is operated, the operation signal will be input to the controlling part 210. The controlling part 210 adjust the photographing light amount by controlling the imaging light source 103 depending on the operation signal that was input.

The observation light amount switch 304 is a switch operated to adjust the emission light amount (observation light amount) of the observation light source 101. The observation light amount switch 304 is provided with, for example, an observation light amount increasing switch "+" for increasing the observation light amount and an observation light amount decreasing switch "−" for decreasing the observation light amount. When one of the observation light amount switches 304 is operated, the operation signal will be input to the controlling part 210. The controlling part 210 adjusts the observation light amount by controlling the observation light source 101 depending on the operation signal that was input.

The jaw holder switch 305 is a switch to move the position of the jaw holder 6 shown in FIG. 13. This jaw holder switch 305 is provided with, for example, an upward movement switch (upward triangle) for moving the jaw holder 6 upward and a downward movement switch (downward triangle) for moving the jaw holder 6 downward. When one of the jaw holder switches 305 is operated, the operation signal will be input to the controlling part 210. The controlling part 210 moves the jaw holder 6 upward or downward by controlling the holder movement mechanism (not shown) depending on the operation signal that was input.

The photographing switch 306 is a switch used as a trigger switch for capturing a 2-dimensional image of the surface of the fundus oculi Ef or a tomographic image of the fundus oculi Ef. When the photographing switch 306 is operated with a menu to photograph a 2-dimensional image selected, the controlling part 210 that has received the operation signal will control the imaging light source 103, and the display part 240A or the touch panel monitor 11. The imaging light source 103 is controlled to emit the photographing illumination light. The display part 240A or the touch panel monitor 11 is controlled to display a 2-dimensional image of the surface of the fundus oculi Ef, based on the video signal output from the imaging device 10 that has detected the fundus reflection light.

On the other hand, when the photographing switch 306 is operated while a menu is selected to capture a tomographic image, the controlling part 210 that has received the operation signal will control the low coherence light source 160, galvanometer mirrors 141A and 141B, and display part 240A or the touch panel monitor 11. The low coherence light source 160 is controlled to emit the low coherence light LO. The galvanometer mirrors 141A and 141B are controlled to scan the signal light LS. The display part 240A or the touch panel monitor 11 is controlled to display a tomographic image of the fundus oculi Ef formed by the image forming part 220 (and image processing part 230), based on the detecting signal output from the CCD 184 that has detected the interference light LC.

The zoom switch 307 is a switch operated to change the angle of view (zoom magnification) for photographing of the fundus oculi Ef. Every time this zoom switch 307 is operated, for example, 45 degree and 22.5 degree of photographing angles of view will be set alternately. When this zoom switch 307 is operated, the controlling part 210 that has received the operation signal controls the variable magnifying lens driving mechanism (not shown). The variable magnifying lens driving mechanism moves the variable magnifying lens 124 in the optical axial direction for changing the photographing angle of view.

The image switch 308 is a switch for operation of switching displayed images. When the image switch 308 is operated during a fundus oculi observation image (a 2-dimensional image of the surface of the fundus oculi Ef based on the video signal from the imaging device 12) is displayed on the display part 240A or the touch panel monitor 11, the controlling part 210 that has received the operation signal will control the display part 240A or the touch panel monitor 11. The display part 240A or the touch panel monitor 11 displays the tomographic image of the fundus oculi Ef. On the other hand, when the image switch 308 is operated during the display of a tomographic image of the fundus oculi on the display part 240A or the touch panel monitor 11, the controlling part 210 that has received the operation signal will control the display part 240A or the touch panel monitor 11. The display part 240A or the touch panel monitor 11 is controlled to display the fundus oculi observation image.

The fixation target switch 309 is a switch for operation of switching the display position of the internal fixation target via the LCD 140 (i.e. the projection position of the internal fixation target in the fundus oculi Ef). When this fixation target switch 309 is operated, the controlling part 210 controls the LCD 140 so as to circulate switching the display position of the internal fixation target, for example, among "fixation position to capture the image including the center region of the fundus oculi (equivalent to the fist projection position of the internal fixation target)", "fixation position to capture the image including macula area (equivalent to the second projection position)", and "fixation position to capture the image including optic papilla (equivalent to the third projection position)". That is, every time the internal fixation target switch 309 is operated, the projection position of the internal fixation target on the fundus oculi Ef is circulated from the first projection position ->the second projection position ->the third projection position ->the first projection position . . . .

The display positions of the internal fixation target corresponding with the above three fixation positions (projection positions), for example, may be preset based on clinical data, or may be set for that eye E (image of the fundus oculi Ef) in advance (that is, the display position may have been stored as examination information for each patient.). This fixation target switch 309 is equivalent to one example of the "operation part" of the present invention.

The fixation target position adjusting switch 310 is a switch operated to adjust the display position of the internal fixation target. This fixation target position adjusting switch 310 is provided with, for example, an upward movement switch for moving the display position of the internal fixation target upward, an downward movement switch for moving it downward, a leftward movement switch for moving it leftward, a rightward movement switch for moving it rightward, and a reset switch for moving it to a certain initial position (default position). The controlling part 210, when having received the operation signal from either of these switches, will control the LCD 140. The LCD 140 is controlled to move the display position of the internal fixation target. This fixation target position adjusting switch 310 corresponds to one example of the "operation part" of the present invention.

The fixation target size switch 311 is a switch for operation of changing the size of the internal fixation target. When this fixation target size switch 311 is operated, the controlling part 210 that has received the operation signal will control the LCD 140. The LCD 140 is controlled to changes the display size of the internal fixation target. The display size of the internal fixation target can be changed, for example, between "normal size" and "enlarged size," alternately. As a result, the size of the projection image of the fixation target projected onto the fundus oculi Ef is changed.

The mode switching knob 312 is a knob rotationally operated to select various types of photographing modes (such as a fundus oculi photographing mode to photograph a 2-dimensional image of the fundus oculi, a B scan mode to perform B scan of the signal light LS, and a 3-dimensional scan mode to have the signal light LS to be scanned 3-dimensionally). In addition, this mode switching knob 312 may be capable of selecting a replay mode to replay a captured 2-dimensional image or a tomographic image of the fundus oculi Ef. In addition, it may be capable of selecting a photographing mode to control so that the photographing of the fundus oculi Ef would be performed immediately after scanning the signal light LS. Control for performing each mode is executed by the controlling part 210.

The controlling feature of the scanning signal light LS by the controlling part 210 and the process feature to the detecting signal from the OCT unit 150 by the image forming part 220 and the image processing part 230 are respectively described below. Furthermore, an explanation regarding the process of the image forming part 220, etc., to the video signal from the fundus camera unit 1A is omitted because it is the same as the conventional process.

Regarding the Signal Light Scanning

Scanning of signal light LS is performed by changing the facing direction of the reflecting surfaces of the Galvano mirrors 141A and 141B of the scanning unit 141 in the fundus camera unit 1A. By controlling the mirror drive mechanisms 241 and 242 respectively, the controlling part 210 changes the facing direction of the reflecting surfaces of the Galvano mirror 141A and 141B, and scans the signal light LS on the fundus oculi Ef.

Once the facing direction of the reflecting surface of the Galvano mirror 141A is changed, the signal light LS is scanned in a horizontal direction (x-direction in FIG. 1) on the fundus oculi Ef. Whereas, once the facing direction of the reflecting surface of the Galvano mirror 141B is changed, the signal light LS is scanned in a vertical direction (y-direction in FIG. 1) on the fundus oculi Ef. Furthermore, by changing the facing direction of the reflecting surfaces of both Galvano mirrors 141A and 141B simultaneously, the signal light LS may be scanned in the composed direction of x-direction and y-direction. That is, by controlling these two Galvano mirrors 141A and 141B, the signal light LS may be scanned in an arbitrary direction on the xy plane.

Figure 8A:
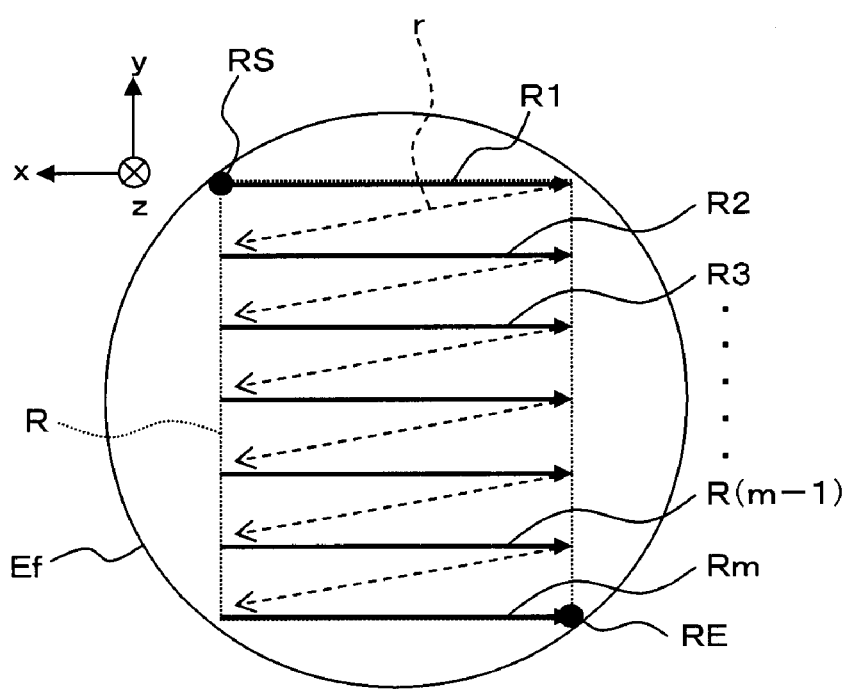
FIG. 8A represents one example of the scanning features of signal light when a fundus oculi is seen from the incident side of the signal light with respect to an eye. In addition.
Figure 8B:
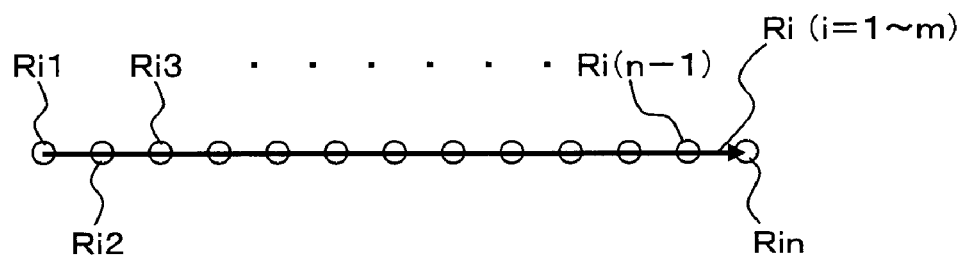
FIG. 8B represents one example of arrangement features of scanning points of each scanning line.

FIG. 8 represents one example of scanning features of signal light LS for forming images of a fundus oculi Ef. FIG. 8A represents one example of scanning features of the signal light LS, when the signal light LS sees the fundus oculi Ef from an incident direction onto the eye E (that is, +direction of z is seen from −direction of z in FIG. 1). Furthermore, FIG. 8B represents one example of arrangement features of scanning points (positions at which image measurement is carried out) on each scanning line on the fundus oculi Ef.

As shown in FIG. 8A, the signal light LS is scanned within a rectangular shaped scanning region R that has been preset. Within this scanning region R, plural (m number of) scanning lines R1 through Rm have been set in the x-direction. When the signal light LS is scanned along each scanning line Ri (i=1 through m), detection signals of interference light LC are to be generated.

Herein, the direction of each scanning line Ri is referred as the "main scanning direction" and the orthogonally crossing direction is referred as the "sub-scanning direction". Therefore, the scanning of the signal light LS in a main scanning direction is performed by changing the facing direction of the reflecting surface of the Galvano mirror 141A, and the scanning in a sub-scanning direction is performed by changing the facing direction of the reflecting surface of the Galvano mirror 141B.

On each scanning line Ri, as shown in FIG. 8B, plural (n number of) of scanning points Ri1 through Rin have been preset.

In order to execute the scanning shown in FIG. 8, the controlling part 210 controls the Galvano mirrors 141A and 141B to set the incident target of the signal light LS with respect to a fundus oculi Ef at a scan start position RS(scanning point R11) on the first scanning line R1. Subsequently, the controlling part 210 controls the low coherence light source 160 to flush the low coherence light L0 for emitting the signal light LS to the scan start position RS. The CCD 184 receives the interference light LC based on the fundus reflection light of this signal light LS at the scan start position RS, and outputs the detection signal to the controlling part 210.

Next, by controlling the Galvano mirror 141A the controlling part 210 scans the signal light LS in a main scanning direction and sets the incident target at a scanning point R12, triggering a flush emission of the low coherence light L0 for making the signal light LS incident onto the scanning point R12. The CCD 184 receives the interference light LC based on the fundus reflection light of this signal light LS at the scanning point R12, and then outputs the detection signal to the controlling part 210.

Likewise, the controlling part 210 obtains detection signals output from the CCD 184 responding to the interference light LC with respect to each scanning point, by flush emitting the low coherence light LO at each scanning point while shifting the incident target of the signal light LS from scanning point R13, R14, - - - , R1 (n−1), R1n in order.

Once the measurement at the last scanning point R1n of the first scanning line R1 is finished, the controlling part 210 controls the Galvano mirrors 141A and 141B simultaneously and shifts the incident target of the signal light LS to the first scanning point R21 of the second scanning line R2 following a line switching scan r. Then, by conducting the previously described measurement with regard to each scanning point R2j (j=1 through n) of this second scanning line R2, a detection signal corresponding to each scanning point R2j is obtained.

Likewise, by conducting a measurement with respect to the third scanning line R3, - - -, the m−1th scanning line R (m−1), the mth scanning line Rm respectively to obtain the detection signal corresponding to each scanning point. Furthermore, the symbol RE on a scanning line Rm is a scan end position in accordance with a scanning point Rmn.

As a result, the controlling part 210 obtains m ×n number of detection signals corresponding to m ×n number of scanning points Rij (i=1 through m, j=1 through n) within the scanning region R. Hereinafter, a detection signal corresponding to the scanning point Rij may be represented as Dij.

Such interlocking control of such shifting of scanning points and the emission of the low coherence light L0 may be realized by synchronizing, for instance, the transmitting timing of control signals with respect to the mirror drive mechanisms 241, 242 and the transmitting timing of control signals (output request signal) with respect to the low coherence light source 160.

As described, when each Galvano mirror 141A and 141 B is being operated, the controlling part 210 stores the position of each scanning line Ri or the position of each scanning point Rij (coordinates on the xy coordinate system) as information indicating the content of the operation. This stored content (scan positional information) is used in an image forming process as was conducted conventionally.

Regarding Image Processing

Next, one example of the process relating to OCT images is described of the image forming part 220 and the image processing part 230.

The image forming part 220 executes the formation process of tomographic images of a fundus oculi Ef along each scanning line Ri (main scanning direction). The image processing part 230 executes the formation process of a 3-dimensional image of the fundus oculi Ef based on these tomographic images formed by the image forming part 220.

The formation process of a tomographic image by the image forming part 220, as was conventionally done, includes a 2-step arithmetic process. In the first step of the arithmetic process, based on a detection signal Dij corresponding to each scanning point Rij, an image in the depth-wise direction (z-direction in FIG. 1) of a fundus oculi Ef at the scanning point Rij is formed.

Figure 9:
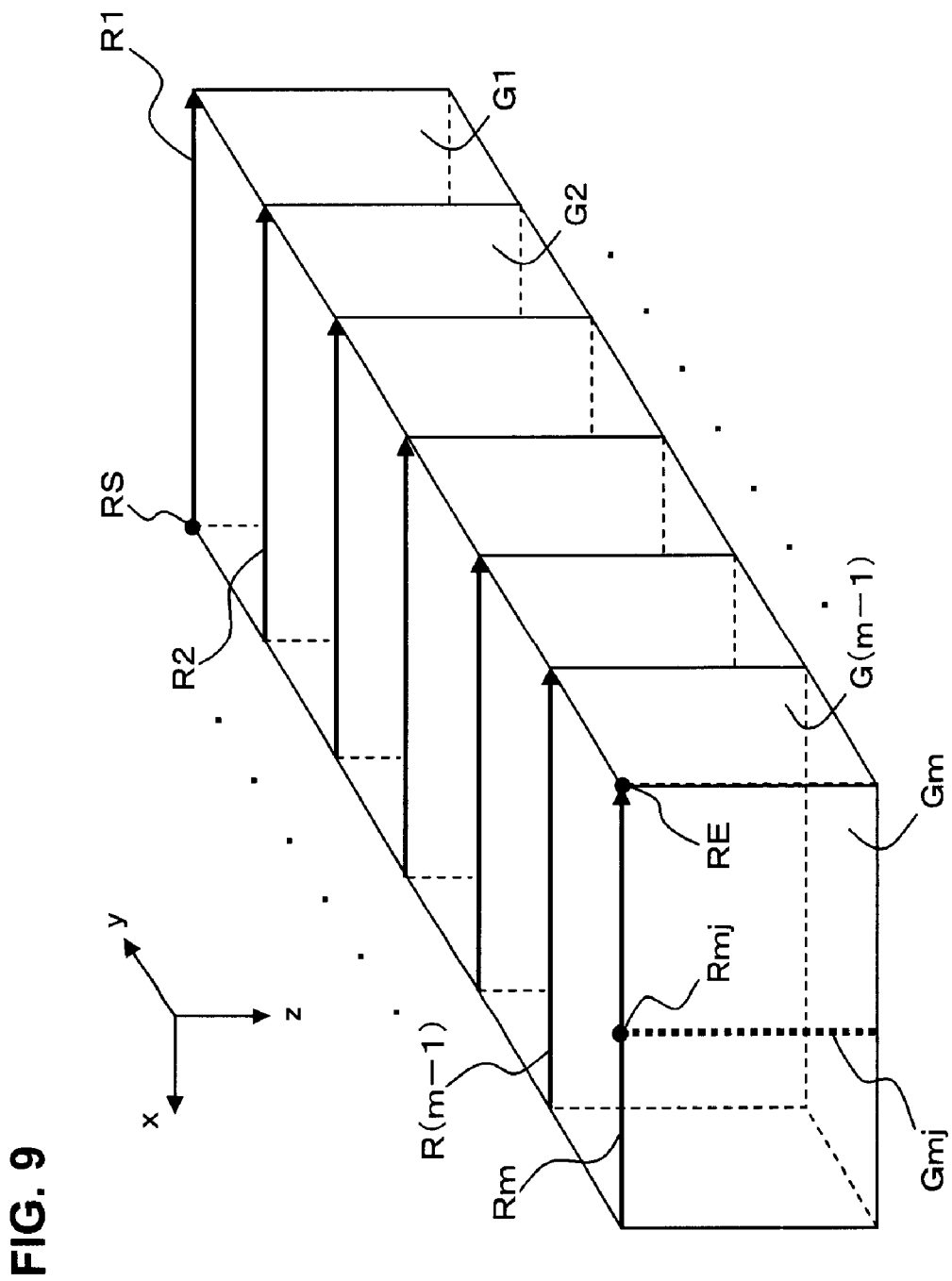
FIG. 9 is a schematic diagram representing one example of the scanning features of signal light and tomographic image features formed along each scanning line in a preferred embodiment of the fundus observation device related to the present invention.

FIG. 9 represents a feature of (a group of) tomographic images formed by the image forming part 220. In the second step of the arithmetic process, with regard to each scanning line Ri, based on the images in the depth-wise direction at the n number of scanning points Ri1 through Rin thereon, a tomographic image Gi of a fundus oculi Ef along this scanning line Ri is formed. Then, the image forming part 220 determines the arrangement and the distance of each scanning point Ri1 through Rin while referring to the positional information (said scan positional information) of each scanning point Ri1 through Rin, and forms a tomographic image Gi along this scanning line Ri. Due to the above process, m number of tomographic images (a group of tomographic images) G1 through Gm at different positions of the sub-scanning direction (y-direction) are obtained.

Next, the formation process of a 3-dimensional image of a fundus oculi Ef by the image processing part 230 is explained. A 3-dimensional image of a fundus oculi Ef is formed based on the m number of tomographic images obtained by the above arithmetic process. The image processing part 230 forms a 3-dimensional image of the fundus oculi Ef by performing a known interpolating process to interpolate an image between the adjacent tomographic images Gi and G (i+1).

Then, the image processing part 230 determines the arrangement and the distance of each scanning line Ri while referring to the positional information of each scanning line Ri to form this 3-dimensional image. For this 3-dimensional image, a 3-dimensional coordinate system (x,y,z) is set up, based on the positional information (said scan positional information) of each scanning point Rij and the z coordinate in the images of the depth-wise direction.

Furthermore, based on this 3-dimensional image, the image processing part 230 is capable of forming a tomographic image of the fundus oculi Ef at a cross-section in an arbitrary direction other than the main scanning direction (x-direction).

Once the cross-section is designated, the image processing part 230 determines the position of each scanning point (and/or an image in the depth-wise direction that has been interpolated) on this designated cross-section, and extracts an image (and/or image in the depth-wise direction that has been interpolated) in the depth-wise direction at each determined position to form a tomographic image of the fundus oculi Ef at the designated cross-section by arranging plural extracted images in the depth-wise direction.

Furthermore, the image Gmj in FIG. 9 represents an image in the depth-wise direction (z-direction) at the scanning point Rmj on the scanning line Rm. Likewise, an image in the depth-wise direction at each scanning point Rij on the scanning line Ri formed by the arithmetic process of said first step may be represented as "image Gij."

Detailed Configuration of the Arithmetic and Control Unit

Detailed configuration of the arithmetic and control unit 200 is described with reference to FIG. 7. Herein, configuration of the controlling part 210 of the arithmetic and control unit 200 is specifically described.

The controlling part 210 is provided with a main controller 211, an image storage part 212, an information storage part 213, and a fixation position calculation part 214.

Main Controller

The main controller 211 comprises a microprocessor 201 or the like and controls each part of the fundus observation device 1 (previously described).

Image Storage Part

The image storage part 212 stores image data of a 2-dimensional image of the surface of the fundus oculi Ef (fundus oculi image) and image data of a tomographic image formed by the image forming part 220. A memory processing of image data to the image storage part 212 and a read processing of image data from the image storage part 212 are performed by the main controller 211. The image storage part 212 is constituted to include a memory device such as a hard disk drive 204.

Information Storage Part

The information storage part 213 includes a memory device such as a hard disk drive 204 storing the fixation position information 213a in advance. Hereinafter, various information included in the fixation position information 213a is explained in detail.

A 2-dimensional X-Y coordinate system is predefined on the display surface of LCD 140 (not shown). This X-Y coordinate system defines a plane parallel to a plane spanned by x coordinates and y coordinates of the x-y-z coordinate system shown in FIG. 1. Herein, scales (lengths of the unit distance) of the two coordinate systems may be either equal or different. In addition, the directions of the coordinate axes of the two coordinate systems may either coincide with each other or not.

Generally, in the case where the scales and the directions of the coordinate axes of the two coordinate systems are both different, the direction of the coordinate axes can be coincident with each other by parallel transfer and rotational transfer, and the scales can be coincident with each other by enlarging/contracting the length of the unit distance of the coordinate axes (in other words, an unique coordinate transformation can be performed.). The fixation position information 213a includes a coordinate conversion equation between the coordinates of the x-y coordinate systems and the coordinates of X-Y coordinate systems.

In addition, the fixation position information 213a includes coordinate values on the X-Y coordinate system indicating the display positions on the LCD 140, for each of the above three fixation positions, that is, the fixation position to capture the image of the peripheral region of the center of the fundus oculi (fixation position for the center of the fundus oculi), the fixation position to capture the image of the peripheral region of macula area (fixation position for macula area), and the fixation position to capture the image of the peripheral region of optic papilla ( fixation position for optic papilla). The coordinate values on the X-Y coordinate system are used for projecting the internal fixation target onto those fixation position.

In addition, the fixation position information 213a includes information indicating the correspondent relationship between the display position of the internal fixation target on the LCD 140 (coordinates on the display surface of the LCD 140) and the center position of the fundus oculi of the image, the image being captured when the eye E is fixated on this internal fixation target (image center point). When the display position of the internal fixation target is changed, the projection position of the internal fixation position on the fundus oculi Ef will be changed accordingly. When the eye E is fixated on this internal fixation target, the position of the fundus oculi Ef through which the optical axis of the optical system of the fundus camera unit 1A passes will be changed. As a result, the center point of the image provided by the imaging devices 10 and 12 or the OCT unit 150 will be changed. In this way, the information is used to change the display position so as to correspond with the center point of the image of the associated internal fixation target. Incidentally, this information may be set for each patient based on information such as the axial length of the eyeball, the center of convolution of the eye E, and so on, or may be set as general information based on clinical data and so on.

Fixation Position Information Calculation Part

The fixation target position adjusting switch 310 and the operation part 240B are operated to specify the desired position on the fundus oculi image Ef' displayed on the touch panel monitor 11 or the display part 240A. The fixation position information calculation part 214 performs the process of calculating the position of the internal fixation target projected onto the fundus oculi Ef, that is, the display position of the internal fixation target on the LCD 140. This process of calculating is based on the position specified on the fundus oculi image Ef' by the fixation target position adjusting switch 310 or the like.

To project the internal fixation target based on this specified position, for example, the following two operations can be applied: (1) projecting the internal fixation target onto the position on the fundus oculi Ef corresponding to the specified position; (2) projecting the internal fixation target onto the position on the fundus oculi Ef such that the image in which the position of fundus oculi Ef corresponding to the specified position is almost centered is captured.

For the case (1) above, the processing of the fixation position information calculation part 214 is specifically described. When the position on the fundus oculi Ef' is specified, the coordinates of this specified position in the above-mentioned x-y coordinate systems will be input from the user interface 240 to the controlling part 210, and will be sent to the fixation position information calculation part 214. The fixation position information calculation part 214 calculates the coordinates of the X-Y coordinate systems corresponding to the coordinates of this specified position. This calculation processing is performed using the coordinate conversion equation (described above) between the coordinates of the x-y coordinate system and the coordinates of X-Y coordinate systems included in the fixation position information 213a. The X-Y coordinate obtained by the coordinate conversion are employed as the display position of the internal fixation target by the LCD 140 for projecting the internal fixation target onto the position on the fundus oculi Ef equivalent to that specified position. Incidentally, in the case where the position is specified on the fundus oculi Ef' by the fixation target position adjusting switch 310 of the operation panel 3a, similar processing will also be performed.

Next, the processing of the fixation position information calculation part 214 in the case of (2) above is specifically described. The fixation position information calculation part 214, in response to the position specified on the fundus oculi image Ef', determines the display position of the internal fixation target on the LCD 140 with reference to the fixation position information 213a so that the specified position is positioned at the center point of the image.

Incidentally, when the projection position of the internal fixation target and the center point of the image almost coincide with each other due to the structure of the optical system of the fundus camera unit 1A or the alignment of the optical system of the fundus camera unit 1A to the eye E, there is no need to distinguish between the processing in the case of (1) above and the processing in the case of (2) above. Therefore, at this time, the fixation position information calculation part 214 can be configured to perform only the processing in either (1) or (2) above.

Example Models of Use

Examples of use of the fundus observation device 1 having the above configuration are described. This fundus observation device 1 is different from the traditional configuration shown in FIG. 11 and FIG. 12, and is provided with the configuration in the optical system in the package of the fundus camera unit 1A, being configured to project the (internal) fixation target onto the fundus oculi Ef. Hereinafter, examples of usage patterns of this internal fixation target are described.

First Model of Use

First, a model of use for switching the position of the internal fixation target projected to the fundus oculi Ef is described. In this fundus observation device 1, the projection position of the internal fixation target can be switched to the fixation position for the center of the fundus oculi, the fixation position for macula area, and the fixation position for optic papilla. In this embodiment, the projection position of the internal fixation target is designed to circulate in the order of the following: the fixation position for the center of the fundus oculi ->the fixation position for macula area ->the fixation position for optic papilla.

When the fixation target switch 309 of the operation panel 3a is operated (pressed), the operation signal will be input from the operation panel 3a to the arithmetic and control unit 200.

The main controller 211, in response to the receipt of this operation signal, controls the display position of the internal fixation target by the LCD 140 so that the internal fixation target is projected onto a projection position next to the current projection position with reference to the fixation position information 213a.

For example, when the fixation target switch 309 is operated with the internal fixation target projected onto the fixation position for optic papilla, the main controller 211 will switch the display position of the internal fixation target displayed on the LCD 140 so that the internal fixation target is projected onto the next fixation position for the center of the fundus oculi.

Incidentally, when the fixation target switch 309 is operated without the internal fixation target displayed on the LCD 140, the main controller 211 is designed to control the LCD 140 to display the internal fixation target at the display position where the internal fixation target is projected, for example, onto the fixation position for the center of the fundus oculi.

Second Model of Use

Next, a model of use for projecting the internal fixation target onto the position specified on the fundus oculi image Ef is described. When the position is specified on the fundus oculi image Ef by the mouse of the operation part 240B or the fixation target position adjusting switch 310 of the operation panel 3a, the operation signal indicating the coordinates (x-y coordinates) of this specified position will be input to the controlling part 210.

The fixation position information calculation part 214 calculates the coordinates on the screen of the LCD 140 (X-Y coordinates). The coordinates correspond to the coordinates of the specified position indicated in this operation signal. The main controller 211 controls the LCD 140 to display the internal fixation target at the position of this calculated X-Y coordinates. As a result, the internal fixation target will be projected onto the position on the fundus oculi region Ef corresponding to that specified position.

Third Model of Use

Next, a model of use for is projecting the internal fixation target such that the position specified on the fundus oculi image Ef is the center point of the image is described. When the position is specified on the fundus oculi image Ef by the mouse of the operation part 240B or the fixation target position adjusting switch 310 of the operation panel 3a. the operation signal indicating the coordinates (x-y coordinates) of this specified position will be input to the controlling part 210.

The fixation position information calculation part 214 calculates the coordinates on the screen of the LCD 140 (X-Y coordinates) with reference to the fixation position information 213a so that this specified position is the image center point. The main controller 211 controls the LCD 140 to project the internal fixation target onto the position of this calculated X-Y coordinates. As a result, the image of the fundus oculi Ef can be captured so that specified position is the image center point (a 2-dimensional image of the surface of the fundus oculi or a tomographic image) with the eye E fixated by this internal fixation target.

Effect and Advantage

The effect and advantage of the fundus observation device 1 as above are as follows.

The fundus observation device 1 related to the present embodiment comprises a LCD 140 for displaying an internal fixation target, a projection optical system (a part of the imaging optical system 120 for forming an optical path of the light emitted from the LCD 140) for projecting the displayed internal fixation target onto the fundus oculi Ef, a controlling part 210 for changing the projection position of the internal fixation target on the fundus oculi Ef by changing the display position of the internal fixation position by the LCD 140, and so on. As a result, a 2-dimensional image of the surface of the fundus oculi or a tomographic image is formed by irradiating the photographing illumination light or signal light LS to the fundus oculi Ef with this internal fixation target projected.

According to such fundus observation device 1, the direction of fixation of the eye E can be easily changed compared to the traditional configuration in which the fixation has been conducted by an external fixation lamp. Therefore, it is possible to easily fixate the eye E in the desired direction, thereby enabling to easily capture any image at the desired position of the fundus oculi Ef.

Incidentally, the LCD 140 is equivalent to one example of the "fixation target displaying part" relating the present invention. In addition, the LCD 140 and the above projection optical system are equivalent of one example of the "fixation target projecting part" relating to the present invention. Furthermore, the controlling part 210 is included in one example of the "projection position changing part" relating to the present invention.

In addition, according to this fundus observation device 1, the internal fixation target can be projected onto the fixation position for the center of the fundus oculi, the fixation position for macula area, and fixation position for optic papilla on the fundus oculi Ef only by operating the fixation target switch 309. As a result, it is possible to easily capture images of the representative observation regions when observing the fundus oculi Ef. The representative observation regions may be images of the center of the fundus oculi, macula area and optic papilla.

Furthermore, the projection position of the internal fixation target can be switched among these three fixation positions only by operating the fixation target switch 309. As a result, it is possible to easily switch the direction of fixation of the eye E.

In addition, this fundus observation device 1, in response to the desired position on the fundus oculi Ef displayed on the display part 240A or the touch panel monitor 11 having been specified, operates to project the internal fixation target onto the position of the fundus oculi Ef equivalent to the specified position. As a result, it is possible to easily fixate the eye E in the desired direction.

In addition, this fundus observation device 1, in response to the desired position on the fundus oculi Ef displayed on the display part 240A or the touch panel monitor 11 having been specified, operates to project the internal fixation target onto the position on the fundus oculi Ef for capturing images of the fundus oculi in which the specified position is the center (a surface image or a tomographic image). As a result, it is possible to easily capture an image in which the desired position of the fundus oculi Ef is the center.

Incidentally, the display part 240A and the touch panel monitor 11 are equivalent of one example of the "displaying part" relating to the present invention, respectively. In addition, as shown in FIG. 1, in the direction perpendicular to the x-y plane (X-Y plane), z coordinate (Z coordinate; not shown) whose positive direction is the depth direction of the fundus oculi Ef is defined. Also, for z coordinate and Z coordinate, their scales may be either equal or different. Hereinafter, X-Y-Z coordinate system and x-y-z coordinate system shall be coincident with each other in the directions of each corresponding coordinate axis and the scale of each coordinate axis shall be equal.

Modified Example

The configuration described above is merely one example to preferably implement the fundus observation device related to the present invention. Therefore, optional modifications may be implemented appropriately within the scope of the present invention.

Although the above fundus observation device 1 is configured so as to be capable of projecting the internal fixation target onto the fixation position for the center of the fundus oculi, the fixation position for macula area, and the fixation position for optic papilla on the fundus oculi Ef, it is sufficient to configure the fundus observation device related to the present invention to be capable of projecting the internal fixation target onto at least one of these fixation positions.

In addition, in the switching operation of the projection position of the internal fixation target, it is sufficient to be capable of switching the projection position of the internal fixation target to two fixation positions of these.

Incidentally, choices for the projection position of the internal fixation target are not limited to these three fixation positions, but it is possible to employ any position on the fundus oculi Ef as a choice.

In addition, while the LCD 140 is used as a fixation target displaying part for displaying a fixation target in the above embodiment, the fundus observation device related to the present invention is not limited to this. For example, any display device such as a plasma display, an organic EL (Electroluminescence) display, and a surface-conduction electron-emitter display can be used other than the LCD (Liquid Crystal Display). In addition, fixation target displaying part in which plurality of LEDs (Light Emitting Diodes) are 2-dimensionally (e.g., like a 2-dimensional array) arranged also can be applied. In that case, the projection position of the fixation target onto the fundus oculi is changed by selectively illuminating the plurality of LEDs.

Figure 10:
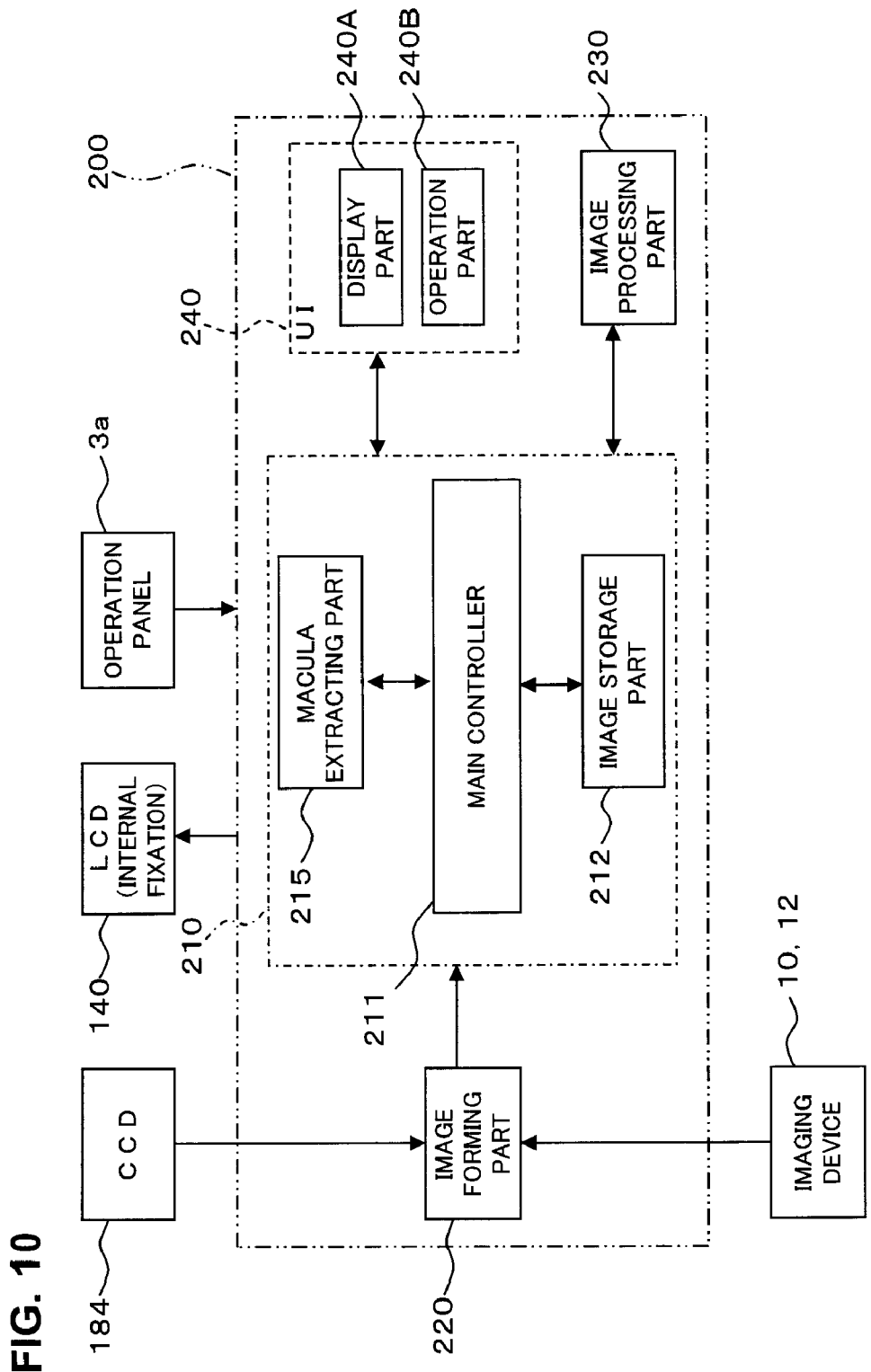
FIG. 10 is a schematic block diagram representing one example of modification of preferred embodiment of the fundus observation device related to the present invention.

The block diagram shown in FIG. 10 illustrates the configuration of a transformation example of the fundus observation device. This fundus observation device comprises a macula extracting part 215 in the controlling part 210 of the arithmetic and control unit 200. This macula extracting part 215 performs the processing for analyzing a tomographic image of a fundus oculi Ef and extracting an image region equivalent to the macula area of the fundus oculi Ef. This macula extracting part 215 acts as an example of the "extracting part" relating to the present invention.

The processing performed by the macula extracting part 215 is more specifically described. First, the image forming part 220 forms (image data of) a tomographic image of a fundus oculi Ef based on the detecting signal from the CCD 184. The macula extracting part 215 determines whether a concave portion equivalent to the macula area exists in the tomographic image by analyzing, for example, a pixel value (luminance value) of this tomographic image.

When a concave portion exists in the tomographic image, the macula extracting part 215 determines the coordinates (x-y coordinates) of the central position of the concave portion (the deepest part of the concave portion) in that tomographic image. The main controller 211 controls the LCD 140 so as to arrange the deepest part of the concave portion at the center of the image by changing the projection position of the internal fixation position onto the fundus oculi Ef. Incidentally, it may be designed to adjust the scanning region of the signal light LS by the Galvano mirrors 141A and 141B so that the deepest part of this concave portion is the center of the image.

When a concave portion does not exist in the tomographic image, the main controller 211 controls the LCD 140 to capture a new tomographic image by changing the projection position of the internal fixation target onto the fundus oculi Ef. The macula extracting part 215 determines whether a concave portion equivalent to the macula area exists in that tomographic image by analyzing this new tomographic image. When one exists, the projection position of the internal fixation target (or the scanning region of the signal light LS) will be changed so that the deepest part of the concave portion is arranged at the center of the image in the same manner as the above case. On the other hand, when no concave portion exists, the main controller 211 captures a new tomographic image by changing the projection position of the internal fixation target again. This processing will be repeated until a concave portion is extracted.

The fundus observation device according to the present embodiment has a retinal camera (unit) as a device that forms two-dimensional images of the fundus oculi surface, while it may have a configuration in which a two-dimensional image of the fundus oculi surface is formed using arbitrary ophthalmological equipment such as a slit lamp biomicroscope, for example.

Moreover, in the above embodiment, the forming process of the images by the image forming part 220 (image forming board 208) and each controlling process are operated by the controlling part 210 (microprocessor 201, etc.), but it can be composed to operate these two processes by one or several computers.

What is claimed is:

1. A fundus observation device comprising:
   fixation target projecting part configured to display a fixation target for fixating an eye and configured to project the displayed fixation target onto a fundus oculi;
   projection position changing part configured to change the display position of said fixation target so as to change the projection position of the fixation target on the fundus oculi,
   first image forming part operable to form a 2-dimensional image of the surface of a fundus oculi with said fixation target projected based on optically captured data;
   second image forming part operable to form a tomographic image of a fundus oculi based on data captured by an optical scan;
   displaying part configured to display the formed 2-dimensional image; and
   operation part configured to specify a position on said displayed 2-dimensional image, wherein said projection position changing part is configured to change the display position of said fixation target to the position specified by said operation part,
   wherein when macula area of the fundus oculi is specified by said operation part, said projection position changing part is configured to determine whether or not the formed tomographic image includes a concave portion, extract an image region of which the concave portion is in the central position, about the tomographic image including the concave portion, and instruct said fixation target projection part to project said fixation target onto the position on the fundus oculi based on the extracted image region as the macula area, wherein said second image forming part is configured to form a new tomographic image to be substantially centered at the concave portion of the fundus oculi of an eye, the eye being fixated by the projected fixation target.

2. A fundus observation device according to claim 1, wherein said projection position changing part is configured to switch said display position among a plurality of positions so as to project said fixation target onto the position when operated by said operation part.

3. A fundus observation device according to claim 1, wherein said second image forming part is configured to form the tomographic image to be substantially centered at the position on the fundus oculi of an eye corresponding to the position specified by said operation part, the eye being fixated by the fixation target whose display position has been changed by said projection position changing part.

4. A fundus observation device according to claim 1, wherein said projection position changing part is configured to extract an image region of which the deepest portion of the concave portion is in the central position, and instruct said fixation target projection part to project said fixation target onto the position on the fundus oculi based on the extracted image region, and said second image forming part is configured to form a new tomographic image to be substantially centered at the concave portion of the fundus oculi of an eye, the eye being fixated by the projected fixation target.

5. A fundus observation device according to claim 1, wherein when the tomographic image does not include a concave portion, said projection position changing part is configured to change the projection position of the fixation image, said second image forming part is configured to form new tomographic image based on the fixation position which is changed, and said projection position changing part is configured to determine whether or not the newly formed tomographic image includes the concave portion.

* * * * *